United States Patent
Shih et al.

(10) Patent No.: US 9,472,717 B2
(45) Date of Patent: *Oct. 18, 2016

(54) METHODS FOR MAKING WATER SOLUBLE QUANTUM DOTS

(71) Applicants: Wei-Heng Shih, Bryn Mawr, PA (US); Giang Au, Sicklerville, NJ (US); Wan Y. Shih, Bryn Mawr, PA (US)

(72) Inventors: Wei-Heng Shih, Bryn Mawr, PA (US); Giang Au, Sicklerville, NJ (US); Wan Y. Shih, Bryn Mawr, PA (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/791,972

(22) Filed: Jul. 6, 2015

(65) Prior Publication Data

US 2015/0311386 A1  Oct. 29, 2015

Related U.S. Application Data

(62) Division of application No. 13/880,880, filed as application No. PCT/US2011/057083 on Oct. 20, 2011, now Pat. No. 9,082,918.

(60) Provisional application No. 61/405,928, filed on Oct. 22, 2010.

(51) Int. Cl.
| | |
|---|---|
| H01L 29/06 | (2006.01) |
| H01L 33/06 | (2010.01) |
| C09K 11/88 | (2006.01) |
| G01N 33/58 | (2006.01) |
| H01L 33/00 | (2010.01) |
| H01L 33/26 | (2010.01) |
| H01L 33/28 | (2010.01) |

(52) U.S. Cl.
CPC ............. *H01L 33/06* (2013.01); *C09K 11/883* (2013.01); *G01N 33/588* (2013.01); *H01L 33/0083* (2013.01); *H01L 33/0091* (2013.01); *H01L 33/26* (2013.01); *H01L 33/28* (2013.01)

(58) Field of Classification Search
CPC .................. H01L 31/035236; H01L 31/0352; H01L 29/7869; H01L 21/02554; H01L 21/00; H01L 21/02565; H01L 45/145
USPC ................................ 257/14, 17, 22; 438/104
See application file for complete search history.

(56) References Cited

U.S. PATENT DOCUMENTS

| | | | |
|---|---|---|---|
| 6,114,038 A | 9/2000 | Castro | |
| 6,426,513 B1 | 7/2002 | Bawendi | |
| 7,402,832 B2 * | 7/2008 | Lee ........................ | B82Y 10/00 257/17 |

(Continued)

OTHER PUBLICATIONS

Carolyn Seydel, "Quantum Dots Get Wet", Science, vol. 300, p. 80, Apr. 4, 2003.

(Continued)

*Primary Examiner* — Quoc Hoang
(74) *Attorney, Agent, or Firm* — Mendelsohn Dunleavy, P.C.

(57) ABSTRACT

A novel quantum dot containing two different metals at non-toxic levels which is capable of narrow bandwidth near infrared emissions at wavelengths of 600-1100 nm. The quantum dot is fabricated via an aqueous method which forms a structure having an inner region of one composition and an outer region of a different composition, wherein the inner region contains at least a first metal and the outer region contains at least a second metal. The quantum dots may be enabled for bioconjugation and may be used in a method for tissue imaging and analyte detection.

20 Claims, 15 Drawing Sheets

(56) References Cited

U.S. PATENT DOCUMENTS

| | | | |
|---|---|---|---|
| 7,750,341 B2 | 7/2010 | Yang et al. | |
| 9,082,918 B2 * | 7/2015 | Shih | C09K 11/883 |
| 2001/0023078 A1 | 9/2001 | Bawendi | |
| 2008/0107590 A1 | 5/2008 | Shih | |
| 2009/0065742 A1 | 3/2009 | Shih | |
| 2009/0286257 A1 | 11/2009 | Shih | |
| 2010/0316797 A1 | 12/2010 | Ying et al. | |

OTHER PUBLICATIONS

S. G. Penn, L. He, and M. J. Natan, "Nanoparticles for Bioanalysis", Curr.Opin. Chem. Bio., pp. 609-615 (2003).

B. V. Enustun and J. Turkevich, "Coagulation of Colloidal Gold", J. Am. Chem. Soc., 85, (21), 3317-3328, (1963).

M. K. Chow and C. F. Zukoski, "Gold Sol Formation Mechanisms: Role of Colloidal Stability", J. Colloid & Interf. Sci., 165, 97-109, (1994).

Fang Zheng, et al, "Synthesis of Highly Luminescent Mn: ZnSe/ZnS Nanocrystals in Aqueous Media" Nanotechnology 21 (2010) 305604 (9pp).

Heesym Yeng, et al, "Water-Soluble Silica-Overcoated Cds: Mn/ZnS Semiconductor Quantum Dots" J. Chem. Phys. 121, 7421 (2004); doi: 10.1063/1.1797071.

Rahul Thakar, et al, "Efficient Emission from Core/(Doped) Shell Nanoparticles: Applications for Chemical Sensing" NANO Letters, vol. 7, No. 11 pp. 3429-3443, 2007.

Dejian Zhou, et al, "A Chelating Dendritic Ligand Capped Quantum Dot: Preparation, Surface Passivation, Bioconjugation and Specific DNA Detection" Nanoscale, vol. 3. pp. 201-211, 2011.

Malgorzata Geszke, et al, "Folic Acid-Conjugated Core/Shell Mn/ZnS Quantum Dots as Targeted probes for Two Photon Fluorescence Imaging of Cancer Cells" Acta Biomaterialia, (2011) vol. 7, pp. 1327-1338.

* cited by examiner

METHODS FOR MAKING WATER SOLUBLE QUANTUM DOTS

CROSS-REFERENCE TO RELATED APPLICATIONS

This application is a divisional of U.S. patent application Ser. No. 13/880,880, filed Apr. 22, 2013, which claims priority to International Application No. PCT/US11/057083, filed Oct. 20, 2011; and U.S. Provisional Application No. 61/405,928, filed on Oct. 22, 2010, the entire disclosure of which is hereby incorporated by reference as if set forth fully herein.

STATEMENT OF GOVERNMENTAL INTEREST

This invention was reduced to practice with Government support under Grant No. W81XWH-09-0701 awarded by the U.S. Army Medical Research and Materiel Command of the Department of Defense; the Government is therefore entitled to certain rights to this invention.

BACKGROUND OF THE INVENTION

1. Field of Invention

The present invention is directed to a method for making photoluminescent water soluble, non-toxic metal, semiconductor nanocrystals that enable biological imaging and analyte detection using near-infrared emissions.

2. Brief Description of the Prior Art

Semiconductor nanocrystals, hereinafter referred to as quantum dots (QDs), with surface bioconjugates have been studied extensively because of their unique optical properties. QDs are inorganic nanoparticles that emit light at a specific wavelength when excited. When light impinges on the QDs, electrons in the valence band are excited to the conduction band, forming short-lived (nanoseconds) electron-hole pairs called excitons that emit photons of a specific wavelength when the electron-hole pairs eventually recombine. The excitonic emission is not as dependent on the excitation light wavelength as that of fluorescent molecules. Therefore it is easier to excite QDs to luminescence than to excite traditional fluorescent molecules that require a specific excitation wavelength. The wavelength of the emitted photons of QDs, however, is specific to and controlled by the composition of the QDs and defect states inside the energy gap.

In the last few years, there has been is an interest in using QDs in biomedical imaging due to advances in surface modification of QDs that have made them accessible for antibody immobilization and detection of antibody-antigen binding. Recent advances enable QDs to be used as imaging markers inside living organisms and as biological markers to find a disease as well as to carry a drug to the exact cell that needs it by immobilizing antibodies on the surface of the QDs. QDs may also be specific to a particular disease and may be tailored to bind only to infected cells. Detection may be carried out either by locating the QDs' particles or by detecting signals emanating from the QDs' particles. For example, luminescence of antibody-coated QDs bound to the cancerous tissue in a mouse helped to locate a tumor (Quantum Dots Get Wet, *Science*, volume 300, p. 80, Apr. 4, 2003). Until now the main biological tags that have been employed are organic fluorophores or radioactive labels (S. G. Penn, L. He, and M. J. Natan, "Nanoparticles for Bioanalysis", *Curr. Opin. Chem. Bio.*, 7, 1-7, (2003)).

The fabrication process of water-soluble luminescent QDs, however, is prohibitively expensive and complex, typically requiring the elimination of QD broadband emissions, thus compromising the commercializability of the QDs.

Additionally, the conventional QDs do not enable near infrared imaging (NIR). Consequently, autofluorescence becomes a challenge for tissue imaging due to spectral overlap. Two major sources of autofluroescence in tissue are elastin and collagen. The fluorescence maxima are in the spectral range between 405 and 460 nm with the excitation source between 270 and 370 nm. It is desirable to have emissions at higher wavelengths for medical imaging in order to reduce or eliminate interference from the autofluorescent signals of tissue.

Conventional QDs also utilize toxic heavy metal elements that are poisonous to the human body, rendering them unsuitable for various bioconjugation and biological applications. For example, Qdot 705™ and Qdot 800™ from Invitrogen made from CdSeTe contain toxic elements.

In view of the aforementioned deficiencies, there is a need to develop enhanced non-toxic highly luminescent QDs capable of producing near-infrared emissions without expressing undesirable broadband emissions.

SUMMARY OF THE INVENTION

In one aspect, the present invention is directed to a quantum dot composition which is capable of a narrow bandwidth emission at a wavelength of 600-1100 nm and can be employed for in vivo applications without creating toxicity concerns. The quantum dot includes an inner region comprising at least a first metal sulfide, selenide or sulfide selenide, and an outer region having a different composition than the inner region, said outer region comprising a second metal sulfide, selenide or sulfide selenide, and a cap.

In a second aspect, the invention is directed to a method for synthesizing quantum dots including the steps of:

a) reacting one or more water-soluble capping agents and a water-soluble salt of a first metal in an acidic aqueous media to form a first reaction product;

b) subsequently adding a water-soluble sulfide to said aqueous media containing said first reaction product to form a capped metal sulfide inner region of said quantum dots; and c) subsequently adding to said aqueous media containing said capped first metal sulfide core, an amount of a water-soluble salt of a second metal in excess of a stoichiometric amount for reaction with said sulfide, to form an outer region of said quantum dot comprising a capped second metal sulfide, said quantum dots having a narrow bandwidth emission in the wavelength range of about 600 nm to about 1100 nm.

In a third aspect, the invention is directed to a method for synthesizing quantum dots including the steps of:

a) reacting one or more water-soluble capping agents, and a water soluble sulfide and an amount of a water-soluble salt of a first metal which is less than a stoichiometric amount for reaction with said sulfide; and b) subsequently adding a water-soluble salt of a second metal and an additional amount of a water-soluble sulfide to the mixture, said quantum dots having a narrow bandwidth emission in the wavelength range of about 600 nm to about 1100 nm.

BRIEF DESCRIPTION OF THE DRAWINGS

FIG. 1(*a*) shows the photoluminescence excitation wavelength (PLE) of the mercaptopropionic acid (MPA) capped ZnSnS QDs of Example 1 having a MPA:(Sn+excess Zn):S molar ratio of 8:5:1, wherein the molar ratio of Sn:Zn=1:4.

DETAILED DESCRIPTION OF THE PREFERRED EMBODIMENTS

Figures 1A, 1B:
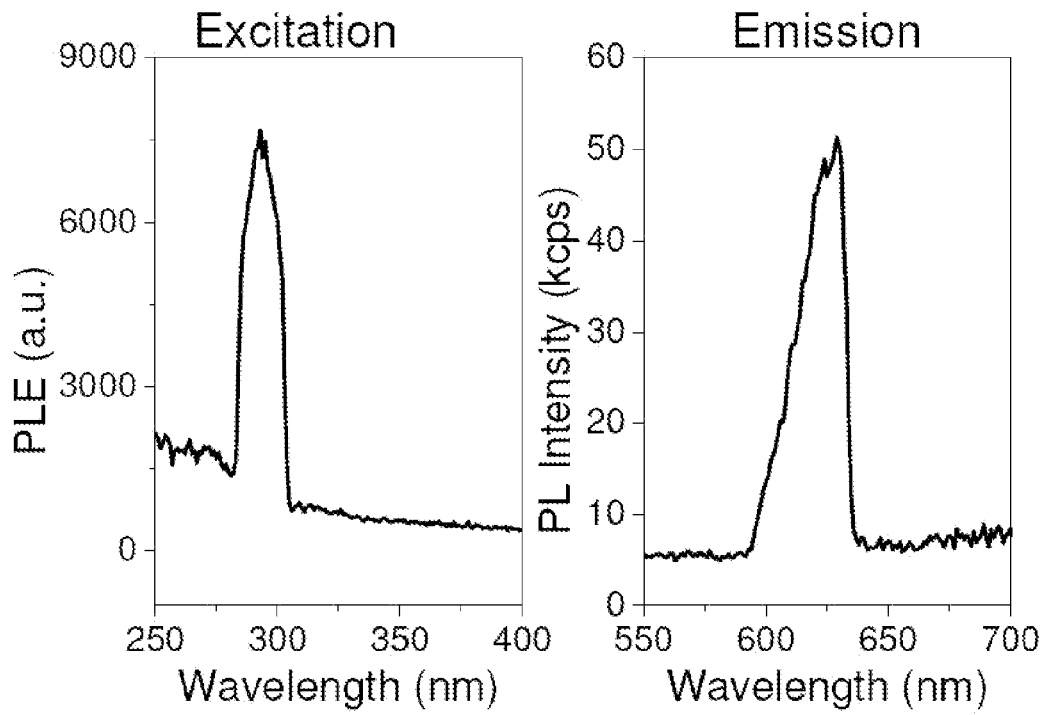
FIG. 1(b) shows the photoluminescence intensity (PLI) of the MPA capped ZnSnS QDs of FIG. 1(a).

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

For purposes of the present invention, "non-toxic metal quantum dots" (hereinafter "QDs") refers to quantum dots that containing metal, including pure metals, metalloids, or metal alloys, wherein the metal does not contain and does not form soluble compounds in an organism, particular the human biological system, in an amount that would be toxic, poisonous or otherwise dangerous to the organism. Whether a particular QD falls within this definition can be determined by application of the solubility constant in water for a particular compound present in the QD to determine the amount of the metal component which would dissolve in the body and comparing this amount to the government regulations specifying the acceptable non-toxic amounts of that particular metal which may be introduced into the body. This definition allows for the presence of essential minerals or metals, such as iron, in quantum dots that provide a beneficial function in an organism's biological system. However, generally safe metals and trace elements, such as chromium, nickel, copper, zinc and iron, present in an excessive amount that becomes harmful to an organism are excluded. Exemplary metals that may become toxic when present in an excessive amount include beryllium, antimony, barium, beryllium, osmium, thallium, vanadium; metals with oxidation states that would be harmful to the human body, such as chromium (IV); radioactive metals, such as actinium, thorium, uranium, radium, transuraniums, silver, thallium, tin and beryllium, such as plutonium or americium, polonium and radioactive isotopes of metals that are not otherwise toxic, such as cobalt-60 or strontium-90; and organometallic compounds, such as dimethyl mercury and tetraethyl lead. Also excluded are quantum dots containing heavy metals that when present in any amount would be toxic or otherwise harmful to an organism, such as arsenic, cadmium, lead and mercury.

For purposes of the present invention, "heavy metals" refer to metals, including pure metals, metal alloys, metalloids, transition metals, lanthanides and actinides, having a high atomic mass and a specific gravity greater than about 5.0 g/cm$^3$.

For purposes of the present invention, "organisms" refers to plants or animals, including mammals, birds, fish, reptiles, insects or combinations thereof.

As defined herein a "narrow bandwidth emission" means a bandwidth of less than 50 nm measured at half of the peak height of the emission.

Furthermore, it must be noted that as used herein and in the appended claims, the singular forms "a", "an", and "the" include plural references unless the context clearly dictates otherwise. Thus, for example, reference to "QD" includes a plurality of QDs and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The present invention pertains to water-soluble, highly luminescent QDs that are capable of near-infrared (NIR) emission. The QDs may be adapted for bioconjugation and may be used to enhance biological imaging and analyte detection. The invention is further directed to novel aqueous synthesis methods for making the aforementioned QDs.

QD Structure

The water-soluble, highly luminescent, non-toxic metal QDs of the present invention may be composed of any suitable nanocrystalline material capable of producing emissions in the NIR spectrum, which is considered to encompass wavelengths from about 600 nm to about 1100 nm. The emission wavelength of the QDs may be from about 600 nm to about 1000 nm, from about 700 nm to about 950 nm, from about 750 nm to about 850 nm or from about 700 nm to about 850 nm.

QDs having excitation wavelengths of up to about 1100 nm may be employed, for example, excitation wavelengths of 300-1100 nm or excitation wavelengths of 350-800 nm are suitable.

The QD composition includes at least two metal compounds and is preferably a metal sulfide (MS), a metal selenide (MSe), or a metal sulfide selenide (MSSe). The QD, an inner region of the QD or an outer region of the QD may have a compositional formula (I)

$$M1_x M2_{(1-x)} Se_y S_{(1-y)} \tag{I}$$

wherein M1 and M2 are different metal elements selected from the metals indicated above as being suitable for QDs. Preferred metals are zinc, tin, nickel, cobalt, iron, copper and manganese, S represents sulfur, Se represents selenium, and x and y define the molar concentrations of the various components. The value of x may be from 0 to less than 1. The value of y may be independently selected and can be from 0 to 1.

The emission bandwidth and NIR emission capability may be controlled by adjusting the composition of the QD, e.g. by adjusting the amount or type of metals M1 and M2 used to synthesize the QD and/or the inner and/or outer regions of the QD. For example, the value of x in the formula (I) above may be selected to provide a QD having a narrow bandwidth emission at a wavelength of from about 600 nm to about 1100 nm. For example, in certain embodiments x may range from about 0.25 to about 0.85 and alternatively, from about 0.4 to about 0.8.

Optionally, the QD may further contain at least one additional element or dopant. In such embodiments, the molar ratio of M1 relative to M2 may be from about 1:9 to about 9:1. Alternatively, the molar ratio of M1 relative to M2 may be from about 3:7 to about 7:3, from about 4:6 to about 6:4.

In certain embodiments of the present invention, the QD may have an inner region and an outer region. The composition of the inner region and the outer region is different. In one embodiment, the inner region is a core and the outer region is a shell surrounding the core. In another embodiment, the outer region is a layer or a plurality of layers, each of which layers may be the same or different in composition. In addition, the outer region may itself be formed as one or more regions or layers having the same or differing compositions.

Capping molecules may be used in the current invention to limit the size of, to protect and/o stabilize the QDs. The capping molecules may also enable bioconjugation of molecules, such as antibodies, streptavidin, lectins, and nucleic acids to the QDs. Suitable capping molecules and methods of application are known to persons skilled in the art. In an exemplary embodiment, the capping molecules may be selected from carboxylated molecules, such as but not limited to mercaptocarboxylic acid (MCA) and 3-mercaptopropionic acid (HSCH$_2$CH$_2$COOH) (MPA), that enable surface immobilization of antibodies and other biomolecules.

In an exemplary embodiment, the molar ratio of (M1+M2):(S+Se) in the QD may be equal to or greater than 1. Alternatively, the molar ratio of (M1+M2):(S+Se) in the QD is from about 1 to about 8, from about 3 to about 7, or from about 4 to about 6. A particularly advantageous ratio of (M1+M2):(S+Se) in the QD is from about 4 to about 5.

The QDs of the present invention may have molar ratios of the capping molecule:(M1+M2) of from about 0.5:3 to about 8:1. Alternatively, the molar ratio of the capping molecule:(M1+M2) is from about 1:1 to about 4:1, or from about 1.4:1 to about 2.5:1. A particularly advantageous ratio is from about 0.5:4 to about 2:1.

The QDs of the present invention have the capability of excitonic photoluminescence in the wavelength range of 600-1100 nm without introducing toxic levels of metals into a living organism. The capability of these QDs to be excited for emission in this wavelength range renders them particularly effective and beneficial for imaging living tissue. The near infrared radiation of the QDs will pass through a sufficient depth of living tissue to enable non-invasive imaging of tissue conjugated to the biomolecules of the QDs. The metal cations and ratios thereof are selected to provide photoluminescence at the desired wavelength.

Exemplary QDs of the present invention have a ratio of capping agent:metal cations:(sulfide and/or selenide) of from about 6-14:2-10:1-4, more specifically, from about 7-10:4-8:1-3, or 7-9:4-7:1-2. Particular embodiments may have ratios of 8:5:1, 10:6:1, 8:6:2 and 8:7:3.

One suitable combination of metals is tin and zinc. When tin and zinc are employed, the ratio of tin:zinc is from about 3:7 to 7:3, or 4:6:6:4 or 5:5. When tin and zinc are employed with MPA or MPS as the capping agent and sulfide, useful ratios of capping agent:metal cations:(sulfide and/or selenide) are from about 6-14:2-10:1-4, more specifically, from about 7-10:4-8:1-3, or 7-9:4-7:1-2. Particular embodiments may have ratios of 8:5:1, 10:6:1, 8:6:2 and 8:7:3.

Methods for Use & Application

The method of use of the present invention may involve use of the capability of the QDs to enhance tissue imaging and for analyte detection. The QDs of the present invention may be directly or indirectly conjugated to a receptor, such as a molecule or biological agent that specifically recognizes and binds to a target moiety, including any molecule, biological agent or receptor expressed on a population of cells. Target moieties may include, but are not limited to, antibodies, or fragments thereof, peptides, hormones, growth factors, cytokines, and any other naturally- or non-naturally-existing ligands, which bind to cell surface receptors. In this manner, the QDs can be targeted to specific cells, biological agents or receptors of interest. Suitable conventional technology may be adopted for this aspect of the QDs of the invention.

Upon excitation, the QD may generate NIR emissions enabling in situ analyte detection and/or deep tissue imaging. Notably, tissue imaging and analyte detection are enhanced when using NIR emissions because light separates from the major absorption peaks of hemoglobin and water, enabling a greater penetration depth than visible light in organs and tissues. This may enable noninvasive deep tissue imaging at a depth typical of NIR penetration, as well as at other depths.

Although the QDs of the present invention may be particularly beneficial for biological applications, such as biomarkers and deep tissue imaging, the QDs may also be useful for a wide variety of other applications, including improving optical properties and conductivity of telecommunication connections, solar and thermal photovoltaic devices as well as other energy harvesting devices and infrared sensing and imaging technologies.

The QDs of the present invention are synthesized from metals to ensure that the QDs are non-toxic in the amounts used in order to ensure safety when used for in vivo imaging of biological systems.

OD Synthesis Methods

The novel QDs of the present application may be synthesized in an aqueous solution using a three step process involving: (1) forming a QD from water-soluble QD precursors; (2) capping the QD with a carboxylated molecules; (3) optionally adjusting the pH of the reaction mixture; and (4) optionally, adding an excess amount of cation to the QD after precipitation. It may also be possible to subsequently replace the carboxylated molecules with other molecules to enhance photoluminescence and stability of the QD. This aqueous synthesis method is effective in producing a substantially clean QD surface enabling a high luminescence yield.

The desired structure of the QD may be achieved using a number of different synthesis methods. In one embodiment, the aqueous QD synthesis process involves mixing and reacting one or more capping molecules with a first metal cation. Subsequently, one or more sulfide or selenide salts is added to the mixture. Optionally, an additional amount of the first metal cation may be added to the mixture after the addition of the sulfide or selenide salt. The components are then allowed to fully react to form an inner region of the QD. When the reaction is complete, an amount in excess of a stoichiometric amount required for reaction with the amount of sulfide and/or selenide salt of a second metal cation is added to the mixture and allowed to react in order to form an outer region. The second metal cation may be added in a single step or in two or more steps. For example, the second metal cation may be added in two or more portions separated by one or more intervals of time. The addition of the excess amount of the second metal cation after the formation of the inner region of the QD allows the formation of a QD having an inner region containing both the first and second metals and an outer region containing only or primarily only the second metal. The pH is preferably maintained throughout the reaction at a particular range around 6.5.

In another embodiment, the aqueous QD synthesis process involves mixing and reacting one or more capping molecules with both a first and second metal cations, with the total combined amount of the first and second metal cations being about stoichiometric amount, based on the amount of sulfide and/or selenide salt employed. Subsequently, one or more sulfide or selenide salts is added to the reaction mixture. Optionally, an additional amount of the first metal cation may be added to the mixture after the addition of the sulfide or selenide salt. The components are then allowed to react to form an inner region of the QD. Then, additional metal cations, preferably additional second metal cations, in excess of the stoichiometric amount required for reaction with the previously provided sulfide and/or selenide salt is added to the reaction mixture, followed by the provision of additional sulfide and/or selenide salt and the mixture is allowed to react to form an outer region of the QD composed of a sulfide and/or selenide of the additional metal. The initial and/or subsequent addition of the second metal cation to the mixture may be added in a single step or in two or more steps. For example, during the latter addition of the second metal cation to the mixture, the second metal cation may be added in two or more portions separated by one or more intervals of time. This step may optionally be repeated one or more times by addition of more metal cation and sulfide and/or selenide salt in order to form additional outer regions or layers. The formation of one or more outer regions or layers may be employed to increase the stability of the QDs. The stability of the QDs may be further improved by subjecting the reaction mixture to a filtration step after formation of the inner region of the QD in order to remove unreacted metal cations that may be present in the reaction mixture.

In another embodiment of the method of the present invention, the aqueous QD synthesis process involves mixing and reacting one or more capping molecules with a first metal cation, followed by addition of one or more sulfide and/or selenide salts to the reaction mixture in order to form the inner region of the QD. Optionally, an additional amount of the first metal cation may be added to the mixture after the addition of the sulfide or selenide salt. Subsequently, a second metal cation and additional sulfide and/or selenide salt is added to the reaction mixture and allowed to react, and excess metal cations, preferably excess second metal cations, are then added to form an outer region. The initial and subsequent addition of the second metal cation may be added in a single step or in two or more steps. For example, during the initial introduction of the second metal cation to the mixture, the second metal cation may be added in two or more portions separated by one or more intervals of time. The sulfide is added before the second metal to minimize the presence of any unreacted first metal which might form by-products as a result of pH adjustment. By adding sulfide and/or selenide in an excess amount compared to the first metal immediately after reaction of the first metal, free first metal present in the solution is minimized Second, the presence of excess sulfide and/or selenide may increase the solubility of one or more components of the QD in acid solutions, ensuring that the QD particle size does not become too large due to particle aggregation. The stability of the QDs may be further improved by subjecting the reaction mixture to a filtration step after formation of the inner region of the QD in order to remove unreacted metal cations that may be present in the reaction mixture.

In another embodiment, the aqueous QD synthesis process involves mixing and reacting one or more capping molecules with a first metal. Subsequently, a sulfide and or selenide salt is added in order to form the inner region of the QD. Optionally, an additional amount of the first metal cation may be added to the mixture after the addition of the sulfide or selenide salt. Then, a second metal is added to and allowed to react with the mixture. Subsequently, an amount of the first metal is added to the mixture and reacted. Afterward, an additional amount in excess of the stoichiometric amount of the second metal is added to form an outer region containing the second metal. Optionally, the initial and/or subsequent addition of second metal cation may be added to the mixture in a single step or in two or more steps. For example, during the initial introduction of the second metal cation, the second metal cation may be added in two or more portions separated by one or more intervals of time. This process employs additional first metal in the QD composition for the purpose of shifting the emission wavelength of the QD to a higher wavelength.

A common theme of the synthesis methods of the present invention is that excess metal cations are added to the reaction mixture. The excess metal cations react with the sulfide and/or selenide salt to form an outer region of the QD around the inner region of the QD. This outer region of the QD may be used to enhance the stability of the QD relative to the same QD without an outer region.

The aqueous synthesis of the QD begins with selecting a starting material that may be any salt of a suitable metal which salt is soluble in water. Suitable metals include any metal that is capable of forming a non-toxic metal QD as defined above. Exemplary metals for use in the QDs of the present invention include zinc, tin, nickel, cobalt, iron, copper and manganese. Exemplary water-soluble metal salts that may be employed are $Zn(NO_3)_2$, $Zn(ClO_4)_2$, $ZnSO_4$, $ZnCl_2$, zinc acetate, $Mn(NO_3)_2$, $Mn(ClO_4)_2$, $MnSO_4$, $MnCl_2$, manganese acetate, $Sn(NO_3)_2$, $Sn(ClO_4)_2$, $SnSO_4$, $SnCl_2$, and tin acetate.

Optionally, any thiol-functionalized molecule with a charged group, preferably on the opposite end from the thiol functionality, may be used as a capping molecule for reacting with the metal salt, as long as the thiol-functionalized molecule is water-soluble. Exemplary thiol-functionalized molecules include 4-aminothiophenol, mercaptosilanes such as 3-mercaptopropyltrimethoxysilane, and similar materials, as well as mercaptocarboxylic acids such as mercaptoacetic acid, mercaptopropionic acid, mercaptosuccinic acid, mercaptobenzoic acid, and mercaptoundecanoic acid. Any concentration of thiol-functionalized molecule may be employed, as long as it is within the solubility limit of the thiol-functionalized molecule in aqueous media. The relative amount of the capping reactants may be varied in order to customize the particle size of the resultant capped QDs. In general, however, the molar ratio of thiol groups to metal may vary from about 1 to about 100. Alternatively, ratios of 1-5 thiol groups per metal atom may be used, or a ratio of about 1.4-2 thiol groups per metal atom.

The precipitated QDs may be further capped with any of the foregoing capping agents, especially mercaptocarboxylic acids, preferably in a one step process. Alternatively, a capping molecule capable of chelating with the metal ions of the QD may be used to minimize the formation of impurity states due to dangling metal ions. These capping molecules may stabilize and limit the growth of the QD particles. 3-mercaptopropionic acid ($HSCH_2CH_2COOH$) (MPA) is preferred as the capping molecule because it has a thiol group that can bind to various metal ions. This follows the example of synthesizing monodispersed gold suspensions using sodium citrate (B. V. Enustun and J. Turkevich, "Coagulation of Colloidal Gold", *J. Am. Chem. Soc.*, 85, (21), 3317-3328, (1963), the disclosure of which is hereby incorporated by reference in its entirety.). Citrate not only reduces the gold but also serves as the capping molecule to stabilize the gold particles. By varying the ratio of citrate to gold, gold particle size is controlled (M. K. Chow and C. F. Zukoski, "Gold Sol Formation Mechanisms: Role of Colloidal Stability", *J. Colloid & Interf. Sci.*, 165, 97-109, (1994)), the disclosure of which is hereby incorporated by reference in its entirety. Without being bound by theory, MPA may play a similar role to cap and stabilize the present QDs.

Additionally, the capping molecule may be selected to enhance the photoluminescent intensity and stability of the QD. For example, MUA may be used to synthesize ZnSnS QDs having a narrow emission wavelength of about 830 nm and is able to sustain a high photoluminescence intensity of about for more than about 2 to 3 days.

The one or more metal salt starting materials and one or more capping molecules may be reacted together to form an initial solution. The solution may be prepared with deionized water or any other suitable solvent. In an exemplary embodiment, the metal salt, in the form of a solution, may be quickly poured into a solution of the capping agent. Alternatively, the metal salt solution may be added to the solution of capping agent at a controlled flow rate to prevent the QDs from growing too large and potentially precipitating out of the solution during the fabrication process. In an exemplary embodiment, the metal salt component may be added over a period of from about 1 to about 20 minutes, preferably, about 10 to about 20 minutes and more preferably, about 10-15 minutes. Optionally, a dopant may also be added to the initial QD solution.

After mixing, one or more water-soluble sulfides and/or selenides may be added to the solution. Any suitable water-soluble sulfide and/or selenide may be used as a reactant in this method. Exemplary water-soluble sulfides that may be employed are sulfides such as $Na_2S$, $K_2S$. Also, sulfide gases, such as $H_2S$, may be bubbled through the aqueous solution. Generally, it is desirable to use about a stoichiometric amount of the sulfide and/or selenide. However, varying the amount of sulfide and/or selenide from a stoichiometric amount can, in some cases, produce desirable variations in the particle sizes of the QDs and thus, it may be useful to use anywhere from 0.1 to 10 times the stoichiometric amount of sulfide and/or selenide, more preferably 0.5 to 5 times the stoichiometric amount of the sulfide and/or selenide, and most preferably about 0.8-1.2 times the stoichiometric amount of the sulfide and/or selenide. The stoichiometric amount is based on the reaction of the sulfide and/or selenide with the metal cations to form the metal sulfide and/or selenide.

Upon mixing, QDs may precipitate from the solution turning the solution to a colloidal suspension. In an exemplary embodiment, when precipitation is complete, an additional amount of one or more metal cations may be added to the QD suspension. Sufficient additional cations may be added to increase the molar ratio of cations to sulfide and/or selenide up to about 7:1 or up to about 6:1.

It may be desirable to adjust the pH of the reaction mixture away from the IEP of metal sulfide and/or selenide using a suitable, water-soluble pH-adjusting agent, before the addition of one or more water-soluble sulfides and/or selenides. Optionally, if additional cation is added, the pH may be adjusted after the addition of the excess cations.

One example of a suitable pH-adjusting agent is ammonium hydroxide. The concentration of the pH-adjusting agent may be varied, as necessary, to produce optimum results. Preferred concentrations of ammonium hydroxide are in the range of about 0.5-2 M and, more preferably, about 0.8-1.2 M, with about 1 M being the most preferred concentration of the ammonium hydroxide as the pH-adjusting agent.

It may also be desirable to adjust the solubility conditions of the mixture from which the QDs are precipitated in order to maximize photoluminescent intensity, enhance photoluminescent stability, and optimize emission and excitation wavelengths. Specifically, the pH, synthesis temperature, QD molar ratio and dopant may be selected to optimize the properties and performance of the QD.

For example, emission wavelength can be increased to the NIR range by increasing the content of a metal cation having a band gap in the NIR range, such as Sn, and/or increasing the QD size, which is affected by the synthesis temperature. In an exemplary capped ZnSnS QD, the Sn content is related to the relative solubility of Sn to Zn, which is governed by the pH. By optimizing the synthesis temperature, fine tuning the nominal Sn/Zn ratio and the way and order in which these elements are added, as discussed above, it is possible to increase the emission and excitation wavelengths.

Preferably, the QDs are precipitated at a neutral pH and synthesized at a low temperature. In one embodiment, the synthesis temperature is about 25° C. to about 100° C., preferably about 25° C. to about 40° C., and most preferably about 25° C. to about 30° C.; the pH level of the mixture during synthesis may be about 5 to about 9, preferably about 6 to about 7.5, and most preferably about 6.5 to about 7.5. Notably, because ZnSnS QDs can be precipitated and maintained at a neutral pH, such as a pH of about 7, it can be safely used for biological applications and synthesized and/or introduced in biological systems.

The process is best performed in oxygen-free environment to avoid the photo-oxidation reaction of sulfur and/or selenium. To prevent further particle growth, the reacted solution may be quenched to freezing point of water and then stored at temperatures of about 0-15° C.

EXAMPLES

Example 1

ZnSnS QDs having a SnS inner region and a ZnS outer region were synthesized using an exemplary method of the present invention.

The QDs were synthesized by first mixing MPA with $Sn^{2+}$ at a pH of about 3. After about 10 minutes, $Na_2S$ was added to this mixture in an amount to achieve a MPA:Sn:S molar ratio of 8:1:1. After about 10 minutes, $Zn^{2+}$ was added to the mixture to achieve a MPA:(Sn+Zn):S ratio of 8:5:1. Since a stoichiometric amount of Sn was used for the amount of sulfide employed, all of the added zinc was in excess of the stoichiometric amount required for reaction of the metal cations with the sulfide. The pH was subsequently adjusted to about 10. After about 10 minutes, the pH was then adjusted to about 12.

FIGS. 1(a)-1(b) show the photoluminescence intensity (PLI) and excitation wavelengths (PLE) for the precipitated QDs. The QDs produced a narrow bandwidth emission at 625 nm. Compared to other QDs, the precipitated ZnSnS QD produced a narrow bandwidth emission, as shown in FIGS. 1(a)-1(b). This edge state emission of is more preferable than broad state emission because color is more defined under the edge state emission. Furthermore, photoluminescence occurred at a wavelength which avoids the problem of autofluorescence.

Example 2

ZnSnS QDs having a ZnSnS inner region and a ZnS outer region with MPA capping molecules were synthesized and tested to compare their emission results with the QDs of Example 1.

The QDs were synthesized by first mixing MPA with $Sn^{2+}$ at a pH of about 3. After about 10 minutes, $Zn^{2+}$ was added into the mixture so that Zn:Sn molar ratio was 1:1. After about 10 minutes, $Na_2S$ was added to the mixture in an amount to achieve a MPA:Sn:S molar ratio of 8:1:1. After 10 minutes, excess $Zn^{2+}$ was added to the mixture in an amount to achieve a MPA:($Zn_{0.5}Sn_{0.5}$+excess Zn):S molar ratio of 8:5:1. The pH was subsequently adjusted to about 10. After about 10 minutes, the pH was then adjusted to about 12.

Figures 2A, 2B:
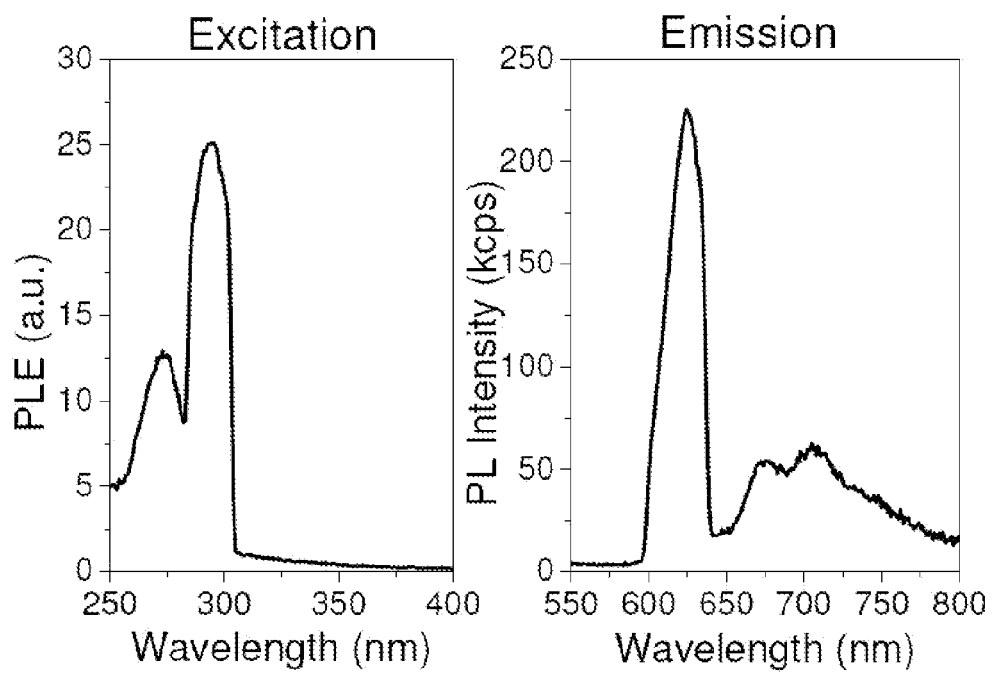
FIG. 2(a) shows the PLE of MPA capped ZnSnS QDs having a MPA: $(Zn_{0.5}Sn_{0.5}+\text{excess Zn})$:S molar ratio of 8:5:1
FIG. 2(b) shows the PLI of the MPA capped ZnSnS QDs of FIG. 2(a).
Figure 3A:
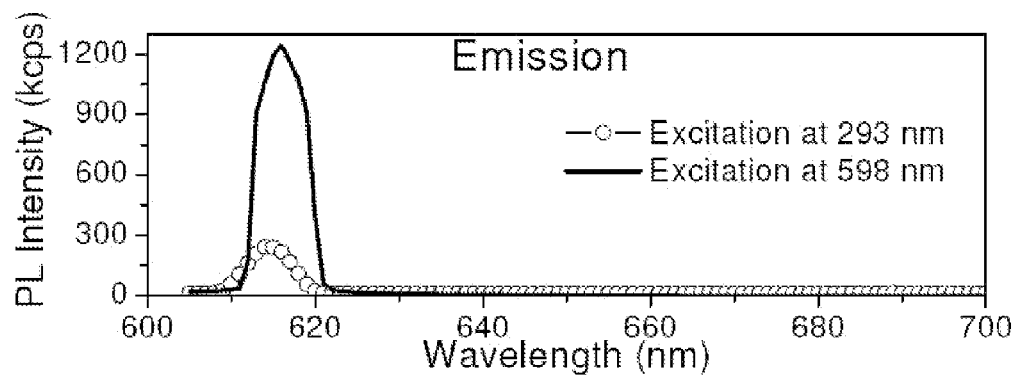
FIG. 3(a) shows the PLI for the QD of Example 2 for two different excitation wavelengths.
Figure 3B:
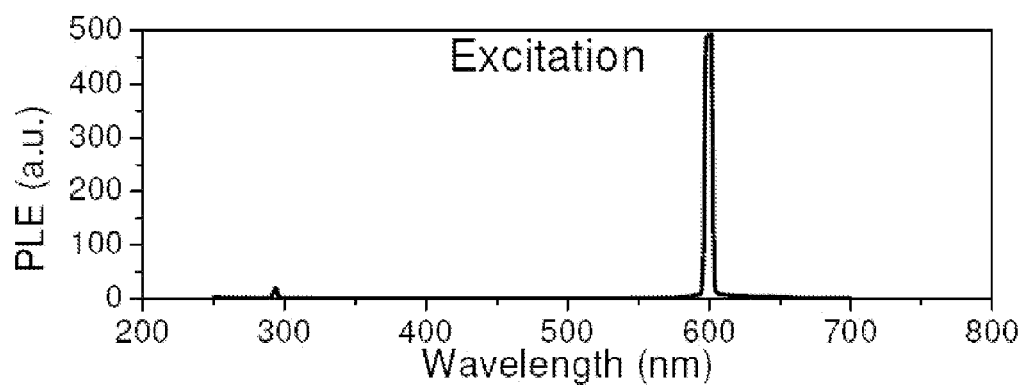
FIG. 3(b) shows the PLE for the QDs of Example 2 at an excitation wavelength of 598 nm
Figure 4A:
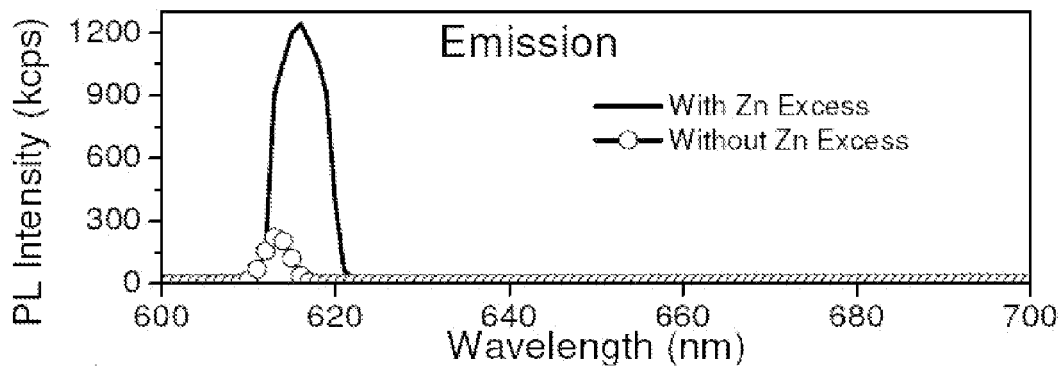
FIG. 4(a) shows the PLI for two different QDs showing the effect of addition of excess zinc to the quantum dot precursor solution.
Figure 4B:
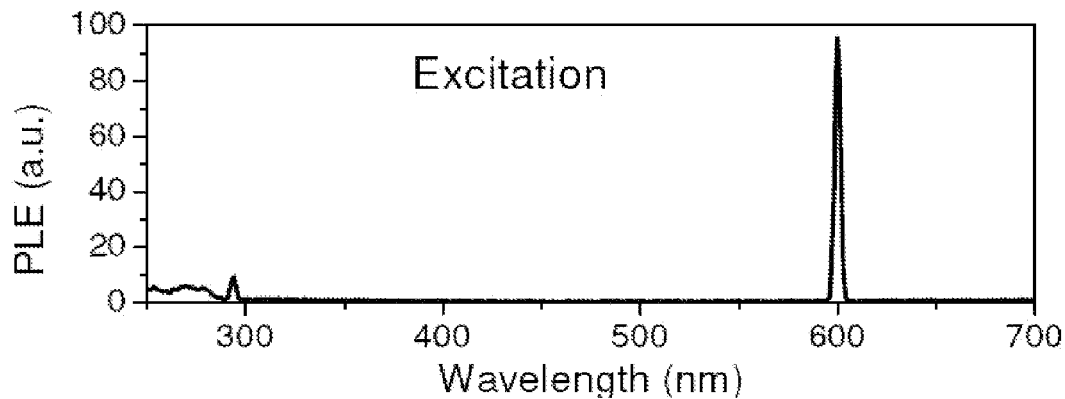
FIG. 4(b) shows the PLE for QDs showing the effect of the addition of excess zinc to the quantum dot precursor solution.

FIGS. 2(a)-2(b) show the photoluminescence intensity (PLI) and excitation (PLE) results of the precipitated QDs of Example 2. The QDs produced a narrow bandwidth emission at about 625 nm Excitation was allowed to run to wavelengths larger than 600 nm and another PLE peak at about 600 nm was found, as shown in FIG. 3(b), producing a significantly higher intensity emission near 625 nm, as shown in FIG. 3(a). The PLI intensity was significantly higher when excess $Zn^{2+}$ was added to the QD precursor mixture as shown in FIG. 4(a). FIG. 4(b) shows the PLE intensity for QDs synthesized with excess $Zn^{2+}$.

Example 3

A plurality of ZnSnS QDs having different molar ratios were synthesized using an exemplary method of the present invention, and the effect of these different MPA:metal cation:S molar ratios on emissions were studied. The ZnSnS QDs had a ZnSnS inner region and a ZnS outer region with MPA capping molecules, wherein the MPA:cation:S molar ratio of the QDs was 8:1:1; 8:2:2; 12:8:2; 8:5:1; 8:6:2; 10:7:2; and 12:8:2.

Figure 5:
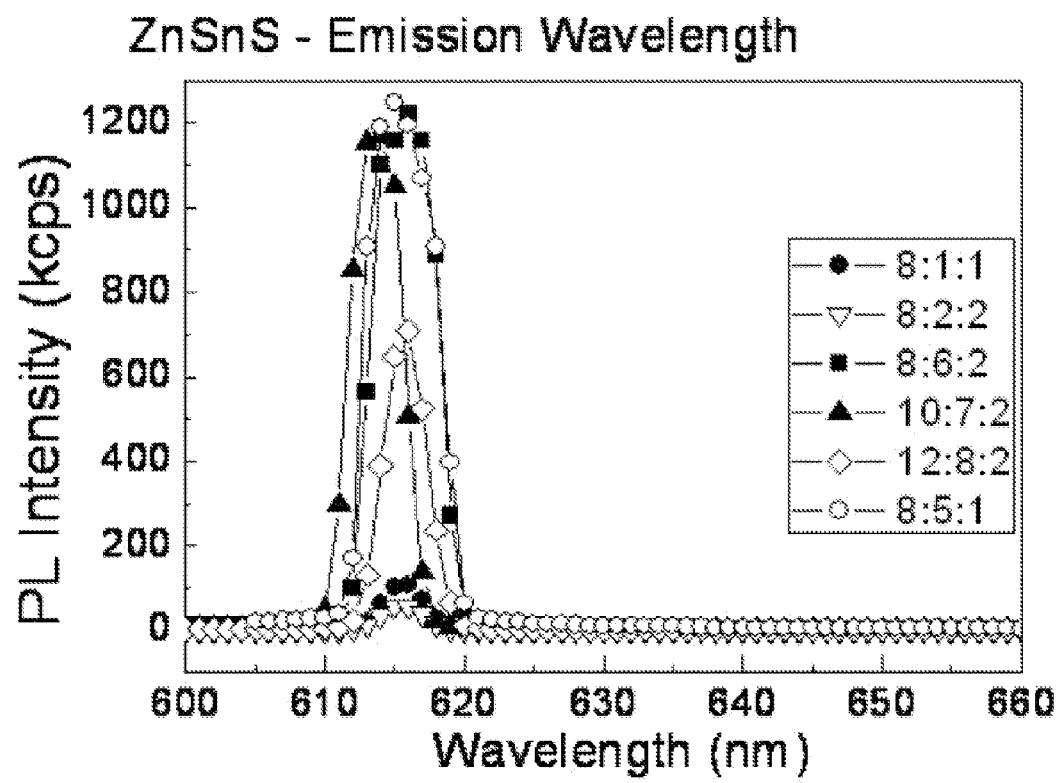
FIG. 5 shows PLI values as a function of time for the various QDs of Example 3.

$Zn_{0.5}Sn_{0.5}S$ QDs having a MPA:cation:S molar ratio of 8:5:1 produced the highest PLI. $Zn_{0.5}Sn_{0.5}S$ QDs having a MPA:cation:S molar ratio of 9:5:2 also produced similar PLI results. As shown in FIG. 5, the other tested QDs had slightly lower PLI. From this study, it was determined that the greater the amount of MPA, Zn and S, the more the emission wavelength shifted to shorter wavelengths. It was also determined that excessive amounts of MPA, Zn and S may not be desirable. For example, MPA:cation:S QDs having a molar ratio of 12:8:2 produced lower PLI emissions than the other tested QDs.

Figure 6:
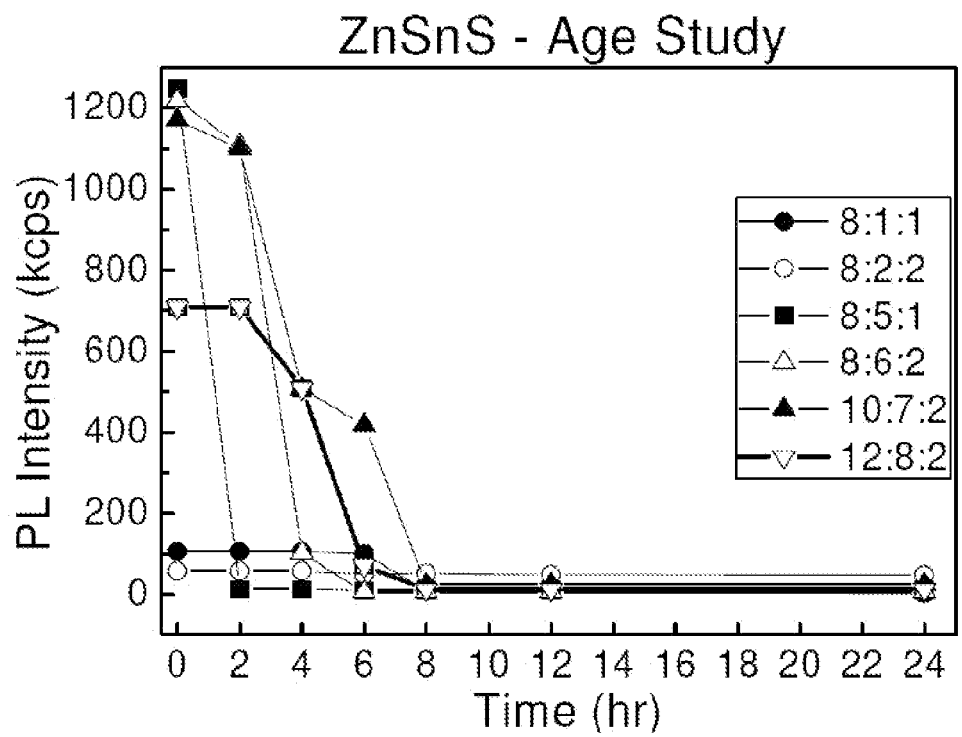
FIG. 6 shows PLI values as a function of time for the various QDs of Example 4 provided with a ZnS outer region, relative to the QDs of Example 3.

FIG. 6 shows that the ZnSnS QDs exhibited a relative short lifetime before the PLI intensity began to decay.

Example 4

To address the stability issue of Example 3, an additional ZnS outer region was added to surround the QD produced by the method of Example 3 in order to improve the overall stability of the QD. The additional ZnS outer region prolonged the lifetimes of the QD as shown in FIG. 6. Therefore, the aqueous synthesis process involved mixing MPA with $Sn^{2+}$ and $Zn^{2+}$ at a pH of about 3. After $Na_2S$ was added to achieve a MPA:($Zn_{1-x}Sn_x$):S molar ratio of 8:1:1, $Zn^{2+}$ was added to the mixture. Subsequently, $Na_2S$ was added to the mixture in an amount to achieve a MPA:($Zn_{1-x}Sn_x$+Zn):S molar ratio of 8:2:2 having a pH of about 3. The pH was then adjusted to pH 10. Excess $Zn^{2+}$ was then added to the mixture, followed by the addition of $Na_2S$, adjusting the pH of the QDs to about 12.

As shown in FIG. 6, the QDs were stable for about 4 hours immediately after synthesis. FIG. 6 further demonstrates that stability improved when MPA and Zn—S amounts were increased. ZnSnS QDs having a MPA:cation:S molar ratio of 10:7:2 had the greatest stability, lasting for about 7 hours. This study demonstrates that the formation of a ZnS outer region surrounding the already formed inner region of the QDs and additional MPA stabilized the Zn on the surface. The results were also consistent with the conclusion that that the greater the amount of MPA, Zn and S, the more the emission wavelength shifted to lower wavelengths.

Example 5

Figure 7:
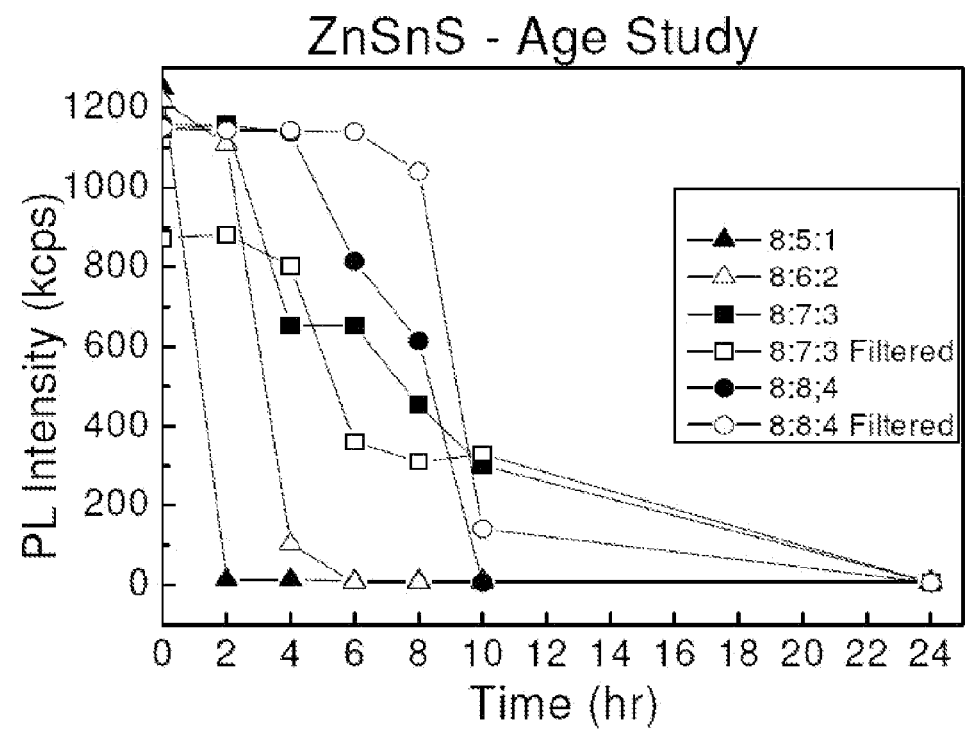
FIG. 7 shows PLI values as a function of time for the various QDs of Example 5 having MPA fixed at 8, provided with an additional ZnS outer region, relative to the QDs of Example 4.
Figure 8:
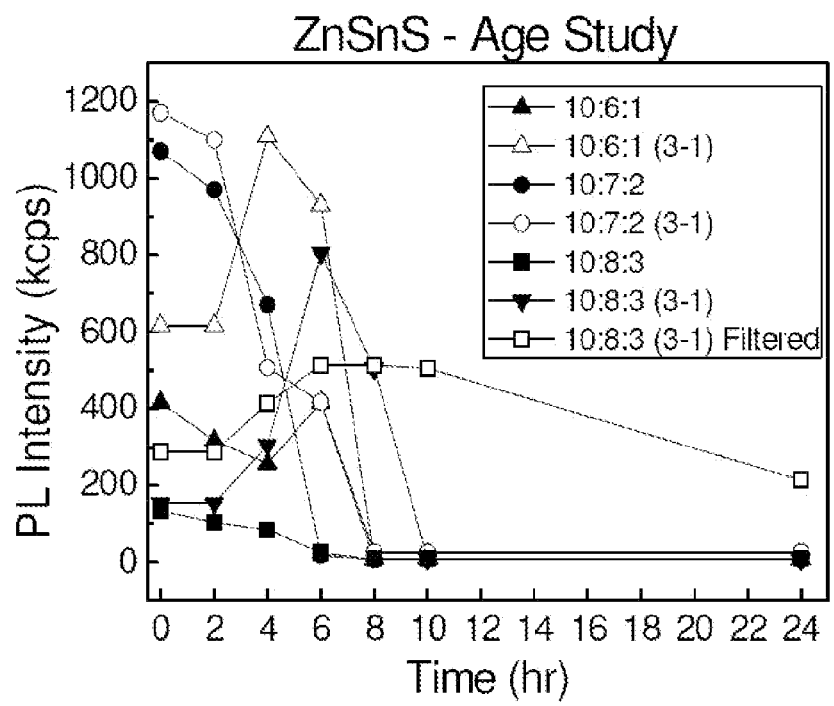
FIG. 8 shows PLI values as a function of time for the various QDs of Example 5 having MPA fixed at 10, provided with an additional ZnS outer region, relative to the QDs of Example 4.

As shown in FIGS. 7-8, it was also determined that the addition of a ZnS outer region further enhances the stability of the QDs. The additional ZnS layers increased photostability of the QDs. For example, as shown in FIG. 7, the PLI of a ZnSnS QDs having a MPA:cation:S molar ratio of 10:6:1 and multiple depositions of ZnS to form the outer region lasted for about 10 hours. FIGS. 7-8 show that when excess Zn was added stepwise, the PLI is more stable. The (3-1) in these figures indicates that 1 mole of 50% Sn+50% Zn was used to form the inner region and that 2 moles of excess Zn were initially added. Finally, the remainder of the Zn was later added to the suspension.

Of the QDs that were studied, ZnSnS QDs having a MPA:cation:S molar ratio of 10:7:2 were found to be particularly stable and produce particularly good PL intensity. ZnSnS QDs having a MPA:cation:S molar ratio of 8:6:2 were also found to possess good PL intensity and QD stability.

Using the same synthesis method, the resultant QD precursor mixture was filtered prior to precipitation to investigate the effects of filtration on QD stability. By filtering the QDs, it was found that stability was further enhanced. For example, filtered QDs having a molar ratio of 8:5:1 and 8:6:2 improved further to about 10 hours. Filtration helped to eliminate free cations in the solution that caused aggregation, such as formation of $Sn(OH)_2$. In addition, free MPA was quickly oxidized. When the amount of MPA was fixed at 10 and subsequently filtered, a similar trend was observed as shown in FIG. 8.

Example 6

A plurality of ZnSnS QDs having different molar ratios was synthesized using another exemplary method of the present invention. The synthesized QDs had a ZnSnS inner region and at least one outer region of ZnS with MPA capping molecules and MPA:cation:S molar ratios of 8:5:1; 8:6:2 and 8:7:3.

The QDs were synthesized by first mixing MPA with $Sn^{2+}$ at a pH of about 3. After about 10 minutes, $Na_2S$ was added to this mixture and allowed to react to form SnS. Additional $Zn^{2+}$ for the $Zn_{1-x}Sn_x$ composition was subsequently added to the mixture, and the pH of the mixture was adjusted to 10. Subsequently, excess $Zn^{2+}$ and $Na_2S$ was added to the mixture to form the ZnS outer region and the pH of the mixture was adjusted to 12. Using this aqueous synthesis method, the SnS was formed prior to the addition of Zn, as well as prior to the formation of the ZnS outer region in order to enhance the stability of the QDs.

Figure 9:
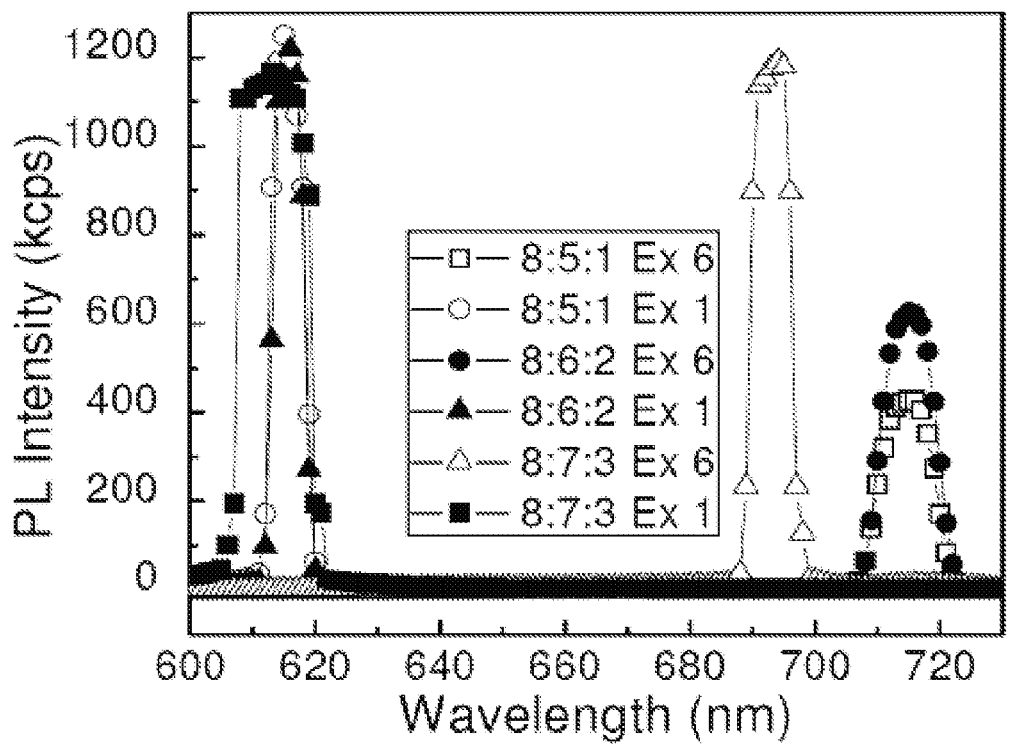
FIG. 9 compares the PLI spectra of the QDs of Example 6 to the QDs of Example 1.

FIG. 9 shows a PLI spectra for the precipitated QDs in comparison to ZnSnS QDs having the same molar ratios of 8:5:1; 8:6:2 and 8:7:3 using the method of Example 2. As shown, the emission wavelengths of the precipitated QDs was about 692-715 nm, which is substantially better than the 620 nm emission wavelengths of the QDs synthesized using the method of Example 2. The excitation wavelength of the QDs, however, was still maintained at about 600 nm.

MPS replacement was experimented with to identify its effect on stability of the QDs For each ratio, the filtered samples showed higher PL intensity than the originals. There were two MPS ratios: 1 mol and ½ mol. For MPS samples, the PL intensities were much lower right after replacement of the MPA. However, the intensity started to increase after one day. This might due to the competition between MPA and MPS on the surface of the QDs. MPS samples showed higher stability, up to 5 days because of the silicon network formation that protect the inner region of these QDs.

Figure 10A:
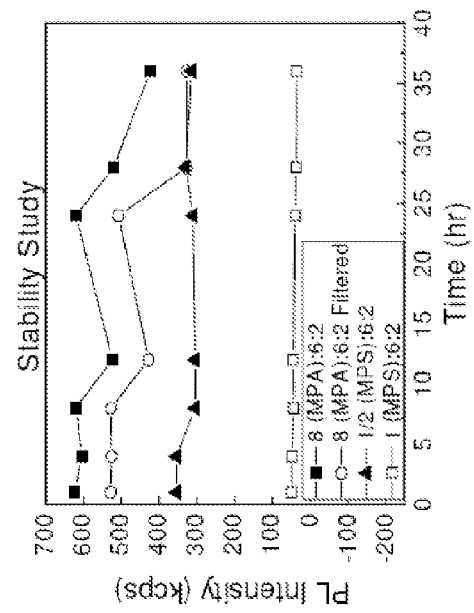
FIG. 10(a)-10(c) show the PLI stability as a function of time of the QDs of Example 6.
Figure 10B:
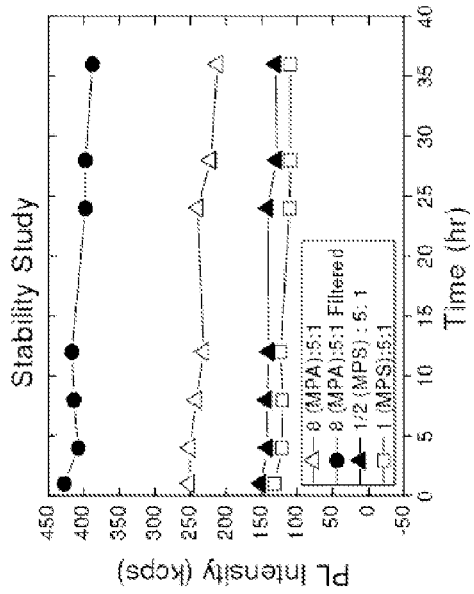
Figure 10C:
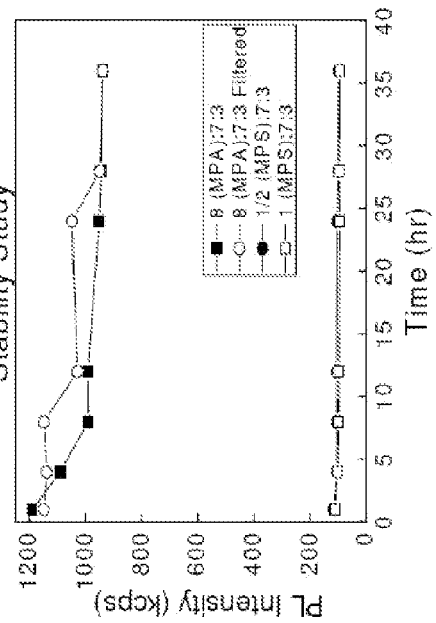
Figure 11B:
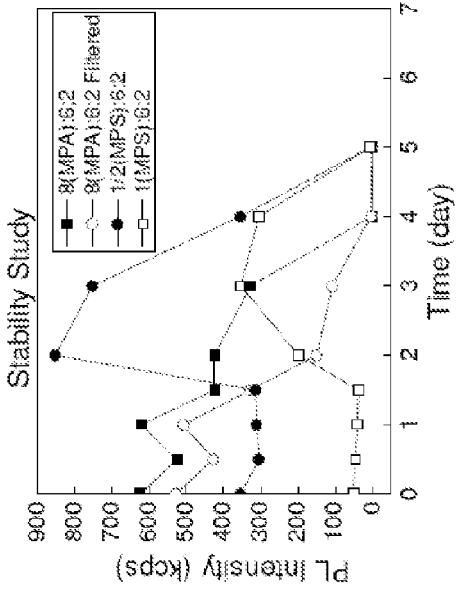
FIG. 11(a)-11(c) show the PLI stability as a function of time of the QDs of Example 6 at a longer time interval than is shown in FIG. 10.
Figure 11A:
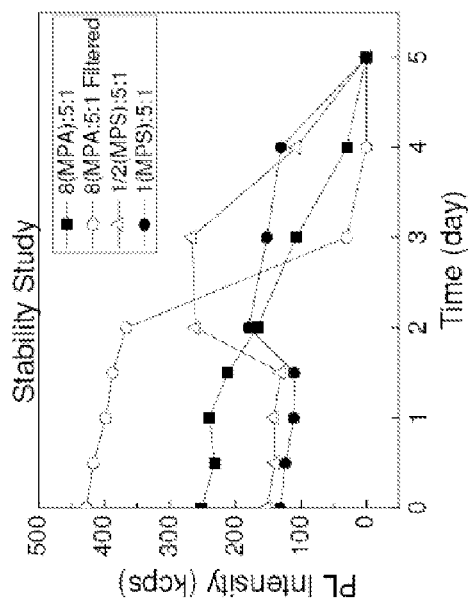
Figure 11C:
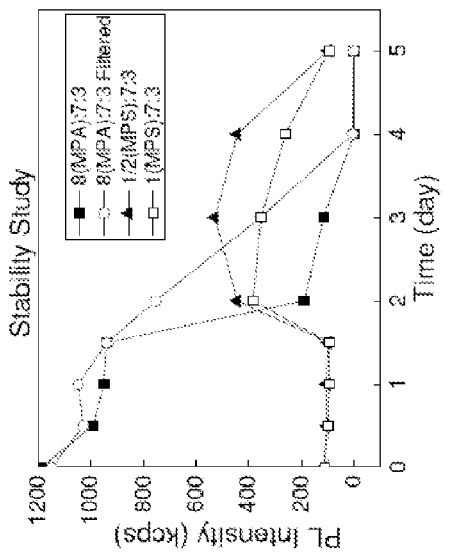

FIGS. 10(a)-10(c) show the PLI stability of these QDs as a function of time. The stability is greatly improved with more ZnS layers giving rise to higher PL. FIGS. 11(a)-11(c) show the PLI stability of these QDs at longer time intervals.

Example 7

Figure 12:
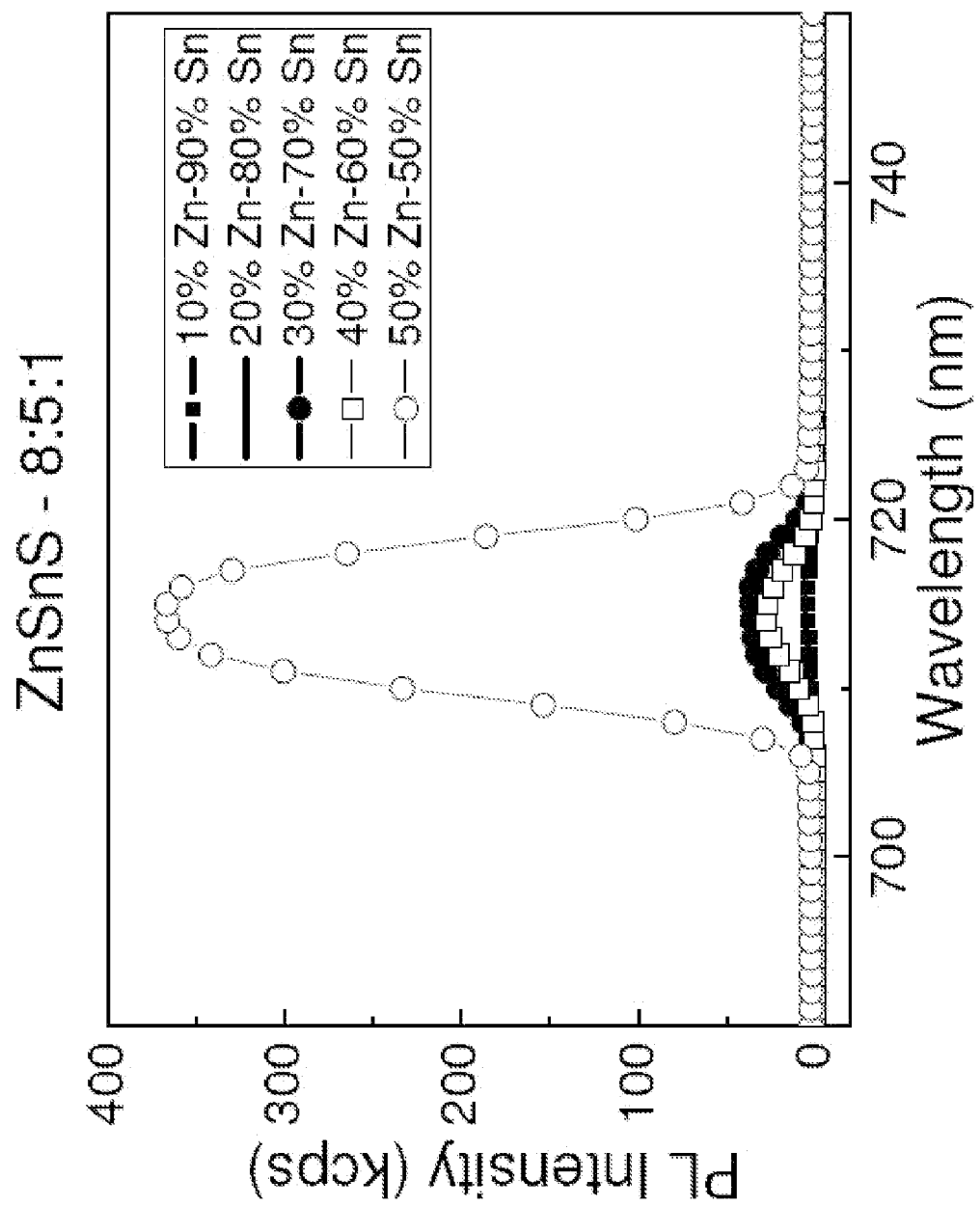
FIG. 12 shows the PLI spectra of the QDs of Example 7.

A plurality of ZnSnS QDs having different percentages of zinc and tin were synthesized using another exemplary method of the present invention. The synthesized QDs with 50% of Zn and 50% of Sn in the inner region showed good PLI values. FIG. 12 shows the PLI spectra of the QDs of Example 7.

Example 8

Figure 13:
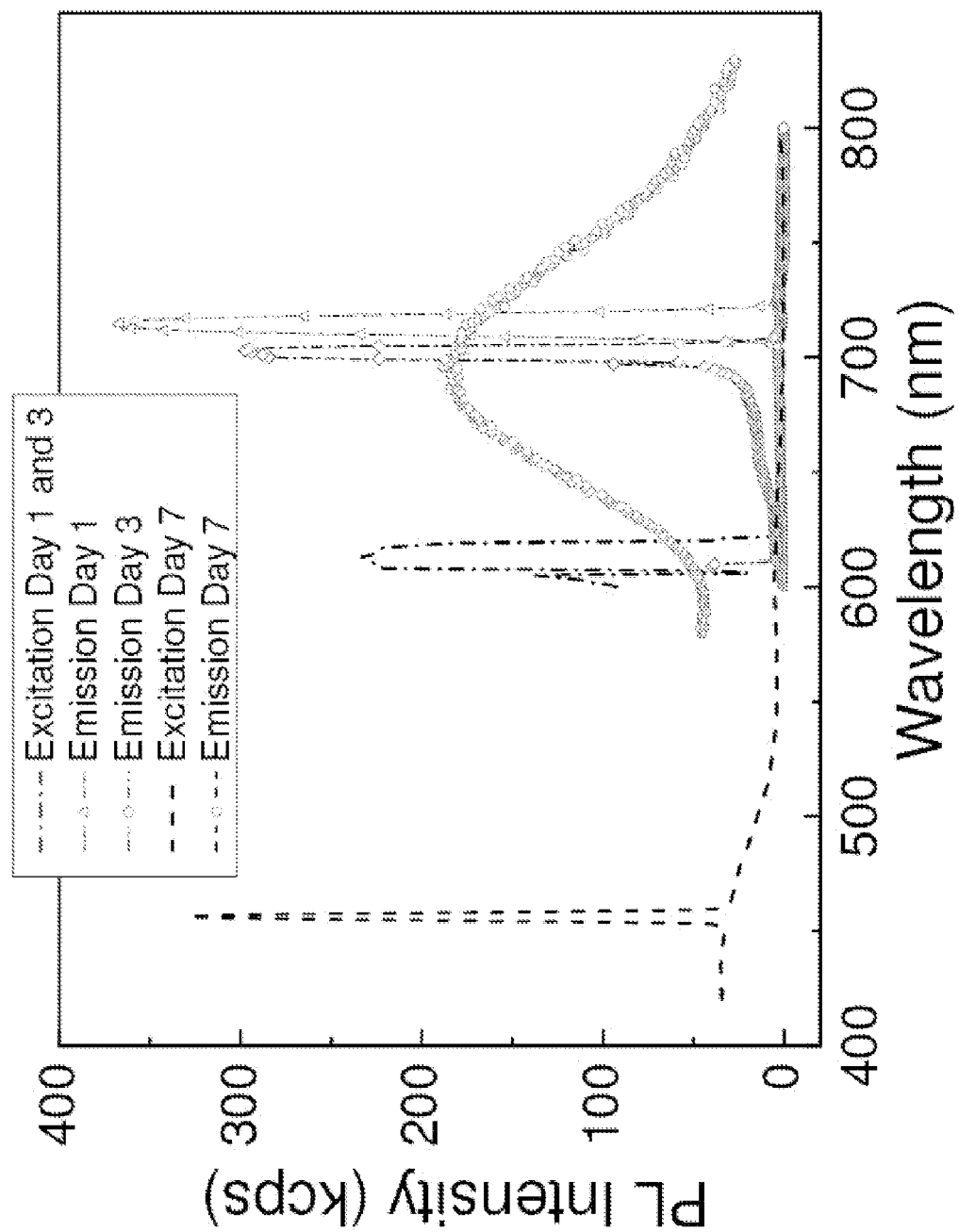
FIG. 13 shows the PLI spectra of ZnSnS mixed with BSA of Example 8.
Figure 14:
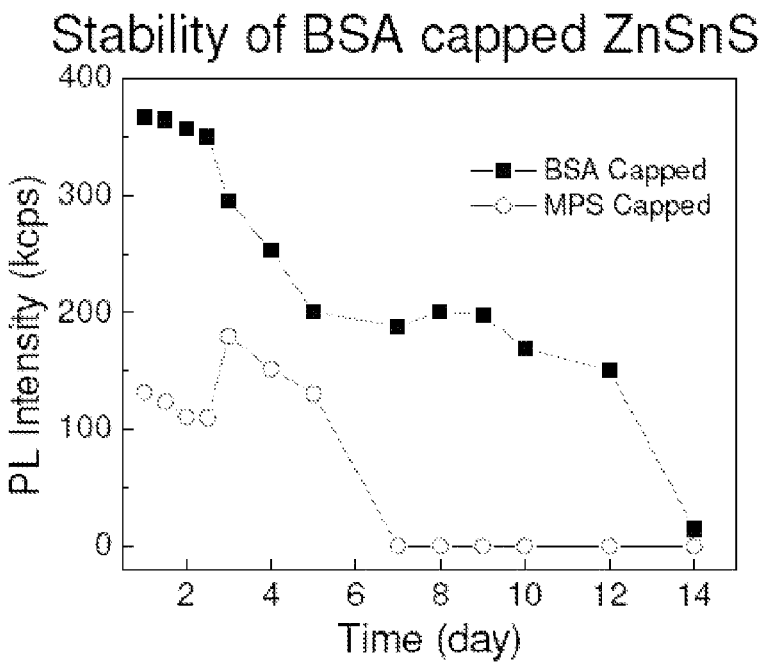
FIG. 14 shows the PLI stability as a function of time for the QDs of Example 8.

The QDs made in previous examples were mixed with BSA. The intensity and stability of the QDs was enhanced. FIG. 13 shows the enhanced stability and PLI for QDs mixed with BSA. FIG. 14 shows the PLI stability of BSA mixed QDs is higher than that obtained by QDs having undergone MPS replacement.

Example 9

ZnSnS QDs were synthesized using another exemplary method of the present invention. The synthesized QD had a ZnSnS inner region and a ZnSnS outer region with MPA capping molecules and a MPA:cation:S molar ratio of 8:4:1.

Figures 15A, 15B:
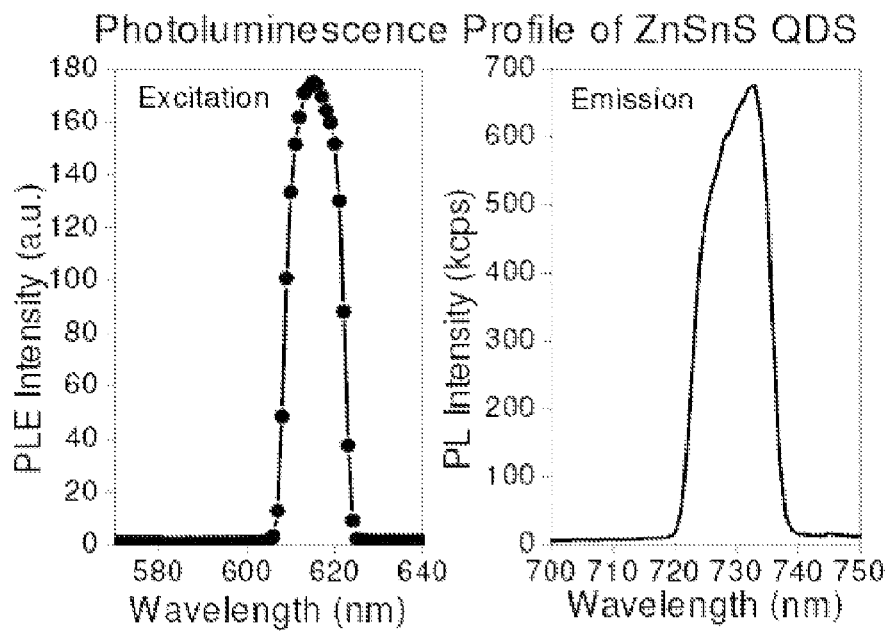
FIG. 15(a) shows the PLE spectra for the QDs of Example 9.
FIG. 15(b) shows the PLI spectra for the QDs of Example 9.
Figure 16A:
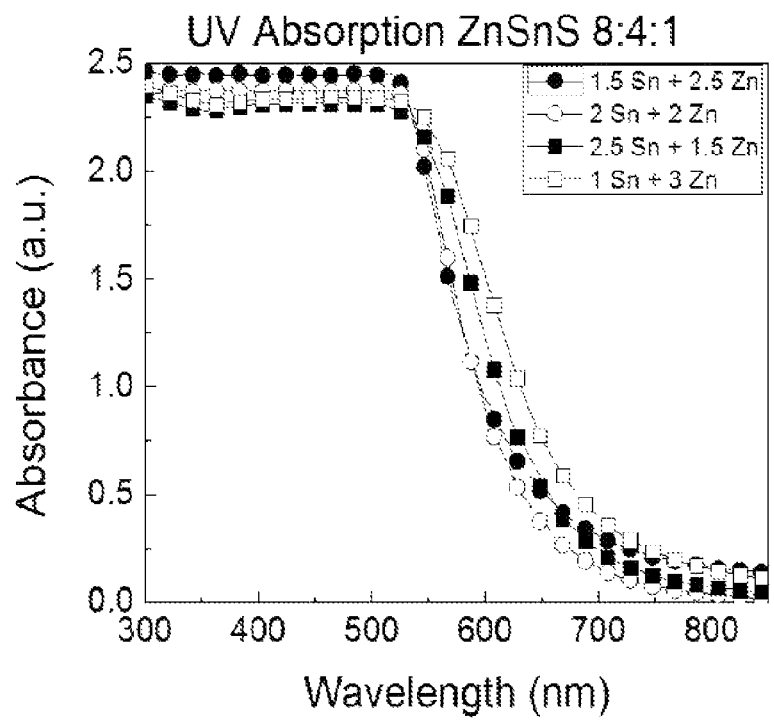
FIG. 16(a) shows the UV absorptions for the QDs of Example 9.
Figure 16B:
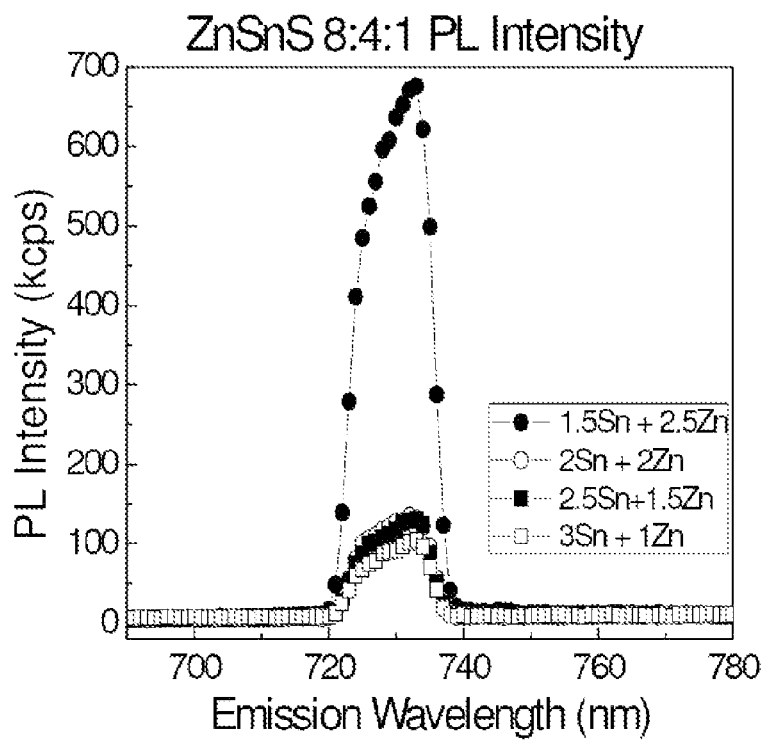
FIG. 16(b) shows the PL intensity differences resulting from variations in the zinc content in the QDs of Example 9.
Figure 17:
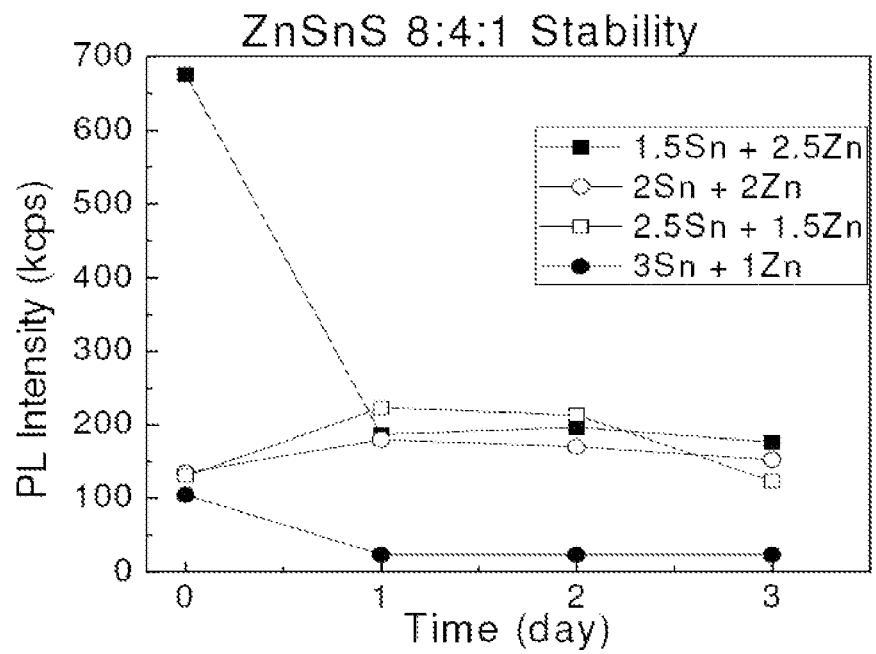
FIG. 17 shows the stability of the QDs of Example 9 as a function of time.

The QDs were synthesized according to an aqueous process that involved adding MPA into DI water and stirring for about 10 minutes. Subsequently, $Sn^{2+}$ was added to the solution at a pH of about 6.5 and followed by the addition of $Na_2S$, forming SnS. Then the remaining $Zn^{2+}$ for the $Sn_{0.5}Zn_{0.5}$ composition of the inner region was added at pH 6.5. Afterward, one mole excess $Sn^{2+}$ was added into the solution followed by an amount of $Zn^{2+}$ in excess of the stoichiometric amount to form an outer region. FIG. 15(b) shows the PL spectra indicating that the emission wavelength was from about 715 nm to about 730 nm. FIG. 15(a) shows the PLE spectra of the QD. FIG. 16(b) shows the intensity differences when the x in the $(Sn_xZn_{3-x})$ changed and 16(a) shows the UV absorption curves, and FIG. 16(a) shows UV absorption as a function of wavelength. FIG. 17 shows the stability of the QDs as a function of time.

The foregoing examples have been presented for the purpose of illustration and description and are not to be construed as limiting the scope of the invention in any way. The scope of the invention is to be determined from the claims appended hereto.

Example 10

Figure 18A:
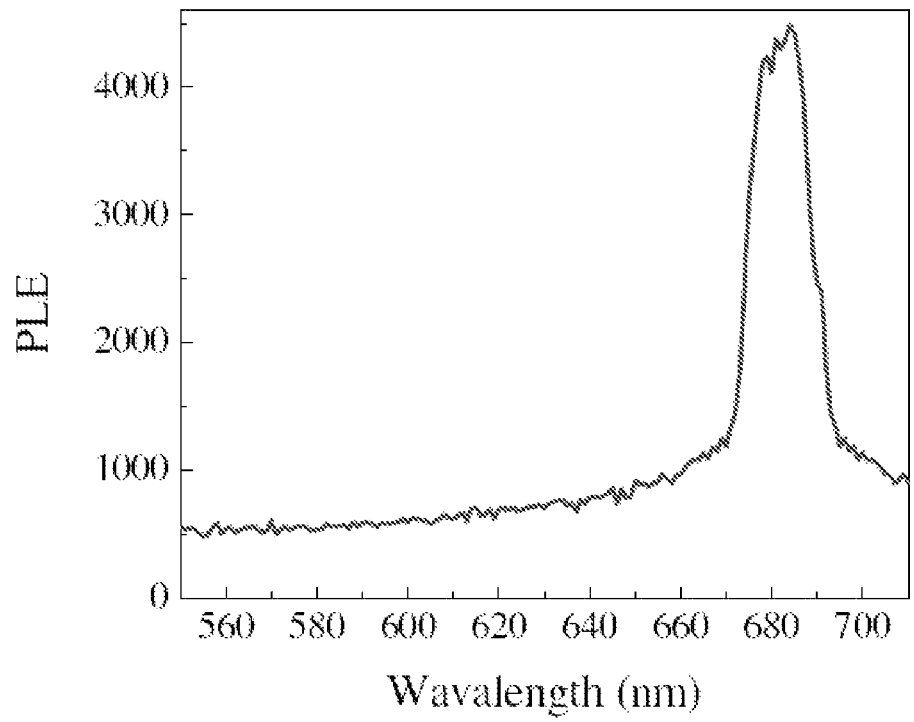
FIG. 18(a) shows the PLE spectra of MPA capped ZnSnS, showing an excitation wavelength is about 690 nm.
Figure 18B:
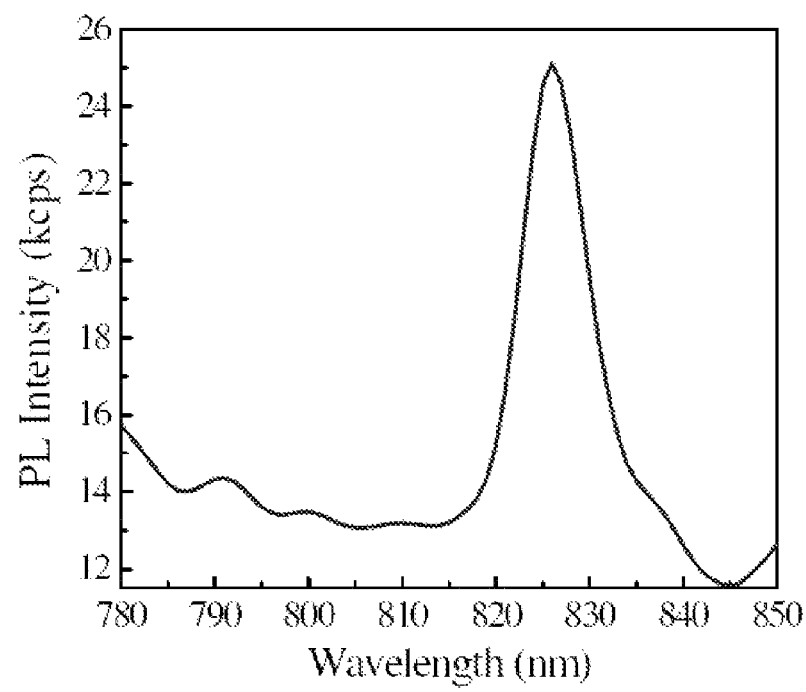
FIG. 18(b) shows the PLI spectra of the MPA capped ZnSnS of FIG. 18(a).
Figure 19A:
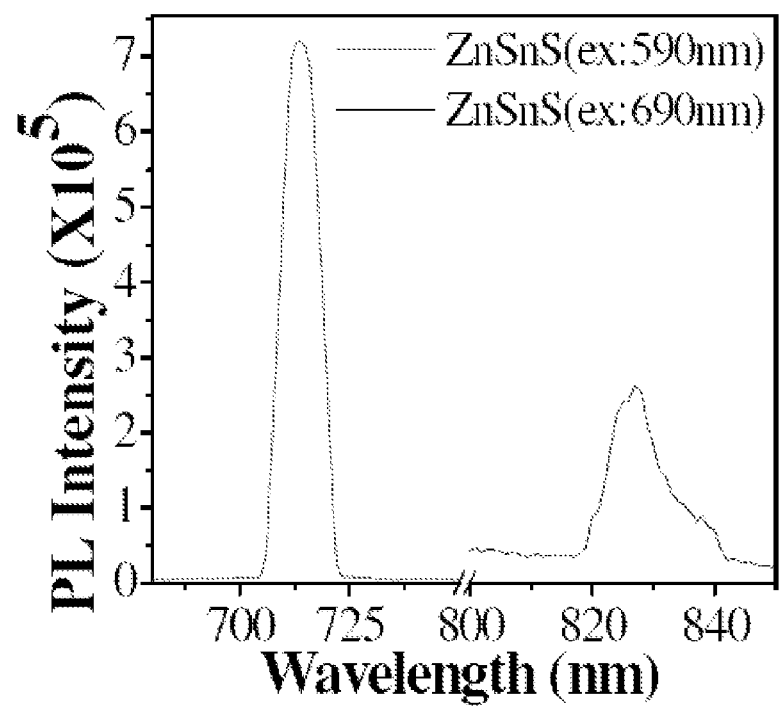
FIG. 19(a) shows the PLI spectra of MPA capped ZnSnS QDs having an excitation wavelength of 590 nm and MUA capped ZnSnS QDs having an excitation wavelength of 690 nm.
Figure 19B:
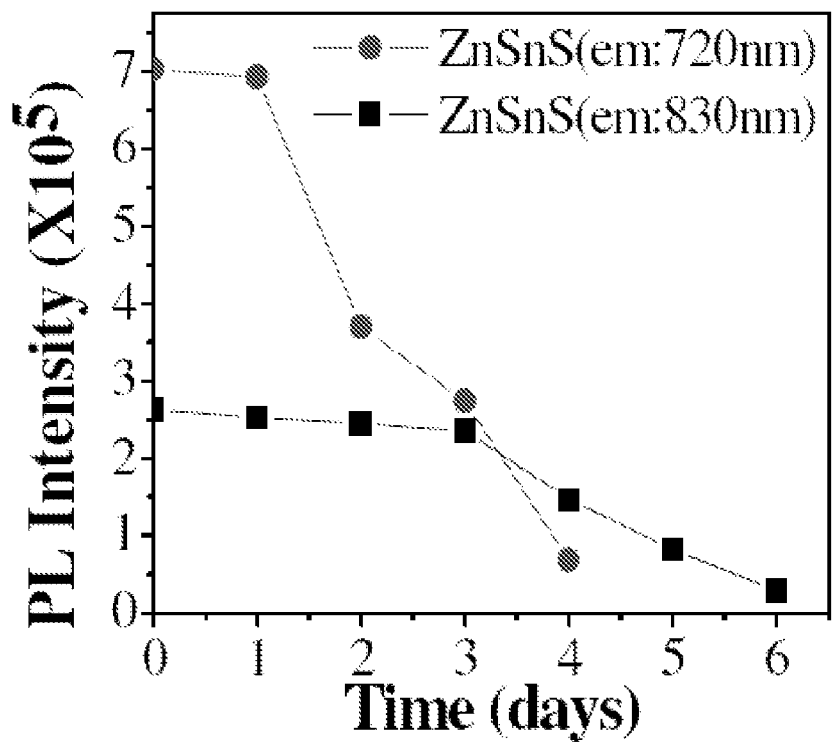
FIG. 19(b) shows the PLI spectra of mercaptoundecanoic acid (MUA) capped ZnSnS QDs having an emission wavelength of about 830 nm and MPA capped ZnSnS QDs having an emission wavelength of about 720 nm, demonstrating the stability of the QDs in water over time.
Figure 19C:
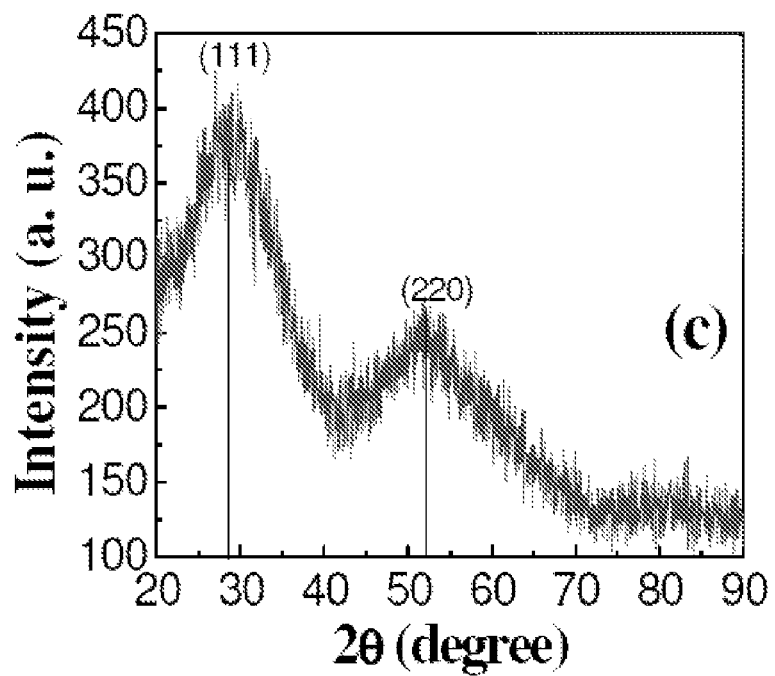
FIG. 19(c) shows XRD patterns for MPA capped ZnSnS QDs having an emission wavelength of about 720 nm.
Figure 19D:
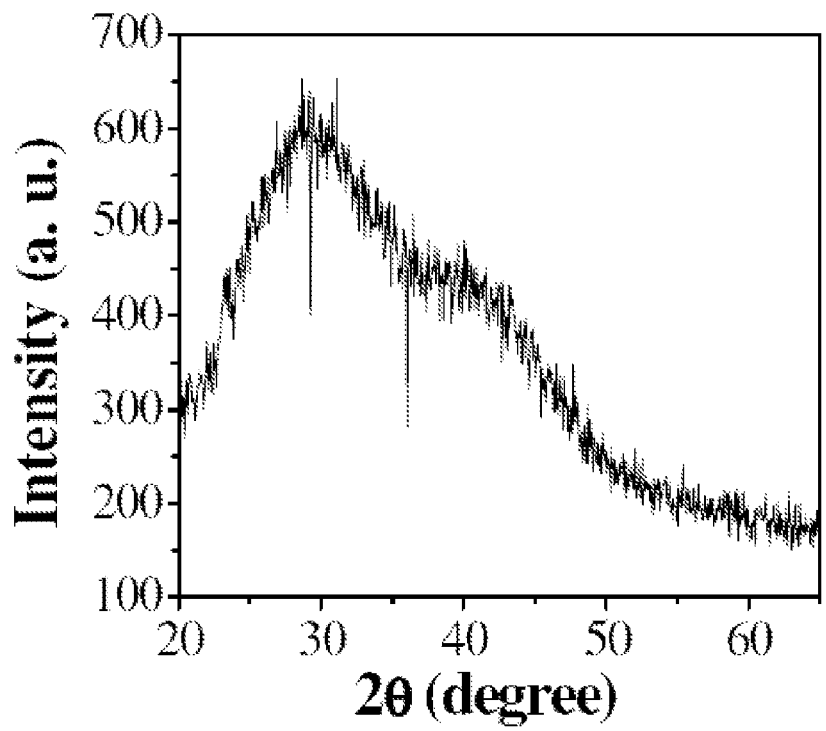
FIG. 19(d) shows XRD patterns for MUA capped ZnSnS QDs having an emission wavelength of about 830 nm.

MPA capped $Zn_{0.5}Sn_{0.5}S$ QDs having narrow bandwidth emission at a wavelength of about 830 nm were synthesized using an exemplary method of the present invention. First about 56 µl of a 3-mercaptopropionic acid solution was added to about 30 ml deionized water. The pH of the solution was then adjusted to about 6 by adding about 1 mL of tetramethylammonium hydroxide [$(CH_3)_4NOH$] having a concentration of about 1M and stirring for 10 min. About 56 µl of about a 50% Tin (II) methanesulfonate $Sn^{2+}$ precursor was added dropwise to the above solution under constant stirring for about 10 min. The pH of the mixture was then adjusted to about 6.5 by adding about 1M nitric acid ($HNO_3$ 200 µl). About 1 ml of sodium sulfide nonahydrate ($S^{2-}$ precursor) having a concentration of about 0.8 M was added to the mixture and stirred for about 10 min, followed by the dropwise addition of about 1 ml of the 0.8 M $Zn(NO_3)_2$ precursor while maintaining the pH at about 7 for about 10 min. This process produced a MPA:(2Sn+1Zn):S QD having a molar ratio of MPA:cation:S of about 8:3:1. The pH was maintained at about 7 during this process. The final suspension was clear with a yellowish tint and had a volume of about 50 ml and a nominal ZnSnS concentration of about 1.6 mM based on the concentration of S. FIGS. 18(a)-18(b) show the excitation and emission spectra of the synthesized QDs.

Example 11

MPA capped ZnSnS QDs having a narrow bandwidth emission at a wavelength of about 830 nm were synthesized using another exemplary method of the present invention. The process involved adding about 56 µl of MPA solution to about 30 ml deionized water. Tetramethylammonium hydroxide was added to adjust the pH to about 6.5, and the mixture was stirred for 10 min. About 56 µl of about a 50% Tin (II) methanesulfonate $Sn^{2+}$ precursor was added in a dropwise fashion with constant stirring for about 10 min. About 1 ml of a sodium sulfide nonahydrate $S^{2-}$ precursor was added, and the mixture was maintained at a pH of about 6.5 and stirred for about 10 min. Then a portion of 1 ml of a $Zn(NO_3)_2$ precursor was added, with about 10 min stirring in between each addition. The pH was maintained at about 6.5 during this process. The final suspension was clear with a brownish color with a volume of about 50 ml and a nominal ZnSnS concentration of about 1.6 mM based on the concentration of S. MPA:(3Sn+2Zn):S QDs having a molar ratio of MPA:cation:S of about 8:5:1 were produced. The photoluminescent intensity of the synthesized QDs was similar to the QDs of Example 10.

Example 12

MUA capped ZnSnS QDs having a narrow bandwidth emission at a wavelength of about 830 nm were synthesized using another exemplary method of the present invention. About 0.873 g of 11-MUA was added to about 50 ml of NaOH having a concentration of about 0.1 M to prepare a MUA precursor having a concentration of about 0.08 M. The whole process was performed in an ice bath so that the mixture temperature was maintained at a temperature of about 0° C. About 8 ml of MUA precursor was added to about 30 ml deionized water. The tetramethylammonium hydroxide was used to adjust the pH to about 10 and the mixture was stirred for about 10 min. About 64 µl of the $Sn^{2+}$ precursor was added in a dropwise fashion with constant stirring for about 10 min. The mixture was then adjusted to a pH of about 6.5 and about 1 ml of the $S^{2-}$ precursor was added and stirred for about 10 min. About 32 µl of the $Sn^{2+}$ precursor was added, and pH was maintained at about 6.5, followed by the dropwise addition of about 2 ml of the $Zn(NO_3)_2$ precursor, wherein the pH was maintained at about 6.5 as well. After about 10 minutes, the pH was raised to about 8, and four portion of about 1 ml $Zn(NO_3)_2$ precursor was added to suspension with about 10-min interval between each step. Finally, in order to increase the stability of QDs, about 18 µl of a MPS precursor was added, and pH was maintained at about 8. The final suspension was brownish color with a volume of about 50 ml and had a nominal ZnSnS concentration of about 1.6 mM based on the concentration of S.

MPA capped ZnSnS QDs were also synthesized using the same method as described in Example 12 with the exception that MUA was replaced with MPA.

In comparison to MPA capped ZnSnS QDs having a MPA:Zn:Sn molar ratio of about 8:2:3, an MPA:cation:S ratio of 8:5:1 and a narrow bandwidth emission at a wavelength of 720 nm, the synthesized MUA capped ZnSnS QDs had a MUA:Zn:Sn molar ratio of about 8:6:3, an MPA:cation:S ratio of 8:9:1, and a narrow bandwidth emission at a wavelength of about 830 nm. The MPA capped and MUA capped QDs both had a core of $Zn_{0.5}Sn_{0.5}S$. The outer shell composition, however, was different.

FIGS. 19(a)-19(d) summarize and compare the properties of the MUA and MPA capped QDs. The narrow bandwidth emission of the ZnSnS QDs at 720 nm and 830 nm, respectively, are highly desirable features. The PL intensity of MUA-capped ZnSnS can be further optimized by changing the synthesis temperature and molar ratio of the QDs. It was found that at 0° C. and at a 8:9:1 MUA:(3Sn+6Zn):S molar ratio, the PL intensity was about 10 times higher than that of MPA-capped ZnSnS QDs.

Example 13 and Comparative Example A

In a cytotoxicity study using human endothelial cells (EA hy926), ZnSnS QDs were compared to commercially available CdSe/ZnS QDs. The results showed that aqueous ZnS QDs have a minimal effect on the cell proliferation process and are therefore suitable for biological system applications. The ZnS QDs were doped with SnS to obtain ZnSnS QDs having an NIR emission. SnS was selected as the doping element because it has a sulfide solubility similar to that of ZnS and because it has a band gap in the NIR range. Furthermore, Sn has no intrinsic toxicity to humans.

Figure 20:
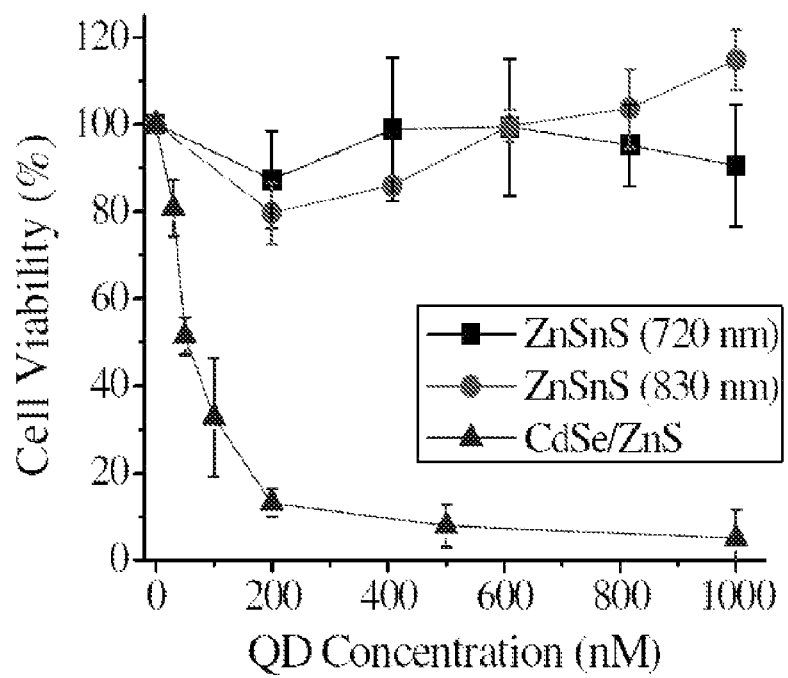
FIG. 20 shows a graph of cell viability as a function of the concentration of different ZnSnS and CdSe/ZnS QDs after about 24 hours incubation in an MTS assay.

To test the cytotoxicity of the ZnSnS QDs, NIH 3T3 cells were seeded at a density of about $2\times10^4$ cells/well on 24 well plates. After incubating for about 24 hours, the cells were incubated in the presence of: MPA capped ZnSnS QDs having an emission at about 720 nm, MUA capped ZnSnS QDs having an emission of about 830 nm and Invitrogen CdSe/ZnS QDs having a carboxylated coating at different concentrations in fresh Dulbecco's Modified Eagle Medium (DMEM). NIH 3T3 cells untreated with QDs were used as a control. Cytotoxicity was measured using the CellTiter 96 aqueous one solution cell proliferation assay system according to the manufacturer's protocol after an incubation period of about 24 hours. The cells were exposed to a methoxyphenyl-tetrazolium salt (MTS) compound and incubated for about 4 hours. The colorimetric formazan was quantified using plate readers at 490 nm. The results, shown in FIG. 20, demonstrate that the ZnSnS QDs were not toxic while the Invitrogen Invitrogen CdSe/ZnS QDs were found to be toxic in the concentration range of about 200 to 1000 nM.

What is claimed is:

1. A quantum dot comprising:
   an inner region comprising a first metal sulfide, selenide or sulfide selenide, and
   an outer region having a different composition than the inner region, said outer region comprising a second metal sulfide, selenide or sulfide selenide,
   wherein a molar ratio of (M1+M2):(S+Se) is from 1 to 8 and M1 and M2 are different metal elements and the metal of the second metal sulfide, selenide or sulfide selenide is selected from the group consisting of zinc, tin, nickel, cobalt, iron, copper and manganese; and
   a cap,
   said quantum dot having at least one narrow bandwidth emission in the wavelength range from of about 600 nm to about 1100 nm.

2. The quantum dot as claimed in claim 1, wherein the inner region comprises a single metal.

3. The quantum dot as claimed in claim 1, wherein the inner region comprises at least two metals.

4. The quantum dot as claimed in claim 1, wherein the inner region comprises one of SnS, SnSe and SnSSe.

5. The quantum dot as claimed in claim 4, wherein the outer region comprises one of ZnS, ZnSe and ZnSSe.

6. The quantum dot as claimed in claim 1, wherein the inner region comprises one of ZnSnS, nSnSe and ZnSnSSe.

7. The quantum dot as claimed in claim 6, wherein the outer region comprises one of ZnS, ZnSe and ZnSSe.

8. The quantum dot as claimed in claim 7, wherein the inner region comprises $Zn_xSn_{1-x}S$, wherein x ranges from 0.1 to 0.9.

9. The quantum dot as claimed in claim 7, wherein the inner region comprises $Zn_xSn_{1-x}S$, wherein x ranges from 0.4 to 0.6.

10. The quantum dot as claimed in claim 1, wherein the cap contains a thiol group.

11. A method for synthesizing quantum dots comprising the steps of:
   a) reacting one or more water-soluble capping agents and a water-soluble salt of a first metal in an acidic aqueous media to form a first reaction product;
   b) subsequently adding a water-soluble sulfide to said aqueous media containing said first reaction product to form a capped metal sulfide inner region of said quantum dots; and
   c) subsequently adding to said aqueous media containing said capped first metal sulfide core, an amount of a water-soluble salt of a second metal in excess of a stoichiometric amount for reaction with said sulfide, to form an outer region of said quantum dot comprising a capped second metal sulfide, said quantum dots having a molar ratio of (M1+M2):(S+Se) is from 1 to 8 and M1 and M2 are different metal elements and a narrow bandwidth emission in the wavelength range of about 600 nm to about 1100 nm.

12. The method of claim 11, wherein said water-soluble salt of a first metal is a tin salt.

13. The method of claim 12, wherein said water soluble salt of a second metal is a zinc salt.

14. The method as claimed in claim 13, wherein a capping agent is selected from 4-aminothiophenol, mercaptosilanes and mercaptocarboxylic acids.

15. A method for synthesizing quantum dots comprising the steps of:
   a) reacting one or more water-soluble capping agents, and a water soluble sulfide and an amount of a water-soluble salt of a first metal which is less than a stoichiometric amount for reaction with said sulfide; and
   b) subsequently adding a water-soluble salt of a second metal and an additional amount of a water-soluble sulfide to the mixture, said quantum dots having a molar ratio of (M1+M2):(S+Se) is from 1 to 8 and M1 and M2 are different metal elements and a narrow bandwidth emission in the wavelength range of about 600 nm to about 1100 nm.

16. The method as claimed in claim 15, further comprising the step of adding an additional amount of a water-soluble metal salt in excess of a stoichiometric amount required to react with the water-soluble sulfide present in the reaction mixture, said additional amount of water-soluble metal salt being added after step (b).

17. The method as claimed in claim 15, wherein the water-soluble salt of a first metal is a tin salt.

18. The method of claim 17, wherein said water soluble salt of a second metal is a zinc salt.

19. The method as claimed in claim 18, wherein a capping agent is selected from 4-aminothiophenol, mercaptosilanes and mercaptocarboxylic acids.

20. The method as claimed in claim 19, wherein an additional amount of the water-soluble salt of the first metal is also added in step (b).

* * * * *